US007220966B2

(12) United States Patent
Saito et al.

(10) Patent No.: US 7,220,966 B2
(45) Date of Patent: May 22, 2007

(54) SYSTEMS AND METHODS FOR INSPECTING COATINGS, SURFACES AND INTERFACES

(75) Inventors: Kozo Saito, Lexington, KY (US); Mohammed I. Hassan Ali, Lexington, KY (US); Akira Numasato, Toyota (JP); Mohammed A. Omar, Lexington, KY (US); Masahito Sakakibara, Okazaki (JP); Toshikazu Suzuki, Aichi (JP); Yasuo Tanigawa, Hebron, KY (US)

(73) Assignee: Toyota Motor Manufacturing North America, Inc., Erlanger, KY (US)

( * ) Notice: Subject to any disclaimer, the term of this patent is extended or adjusted under 35 U.S.C. 154(b) by 147 days.

(21) Appl. No.: 10/987,065

(22) Filed: Nov. 12, 2004

(65) Prior Publication Data

US 2005/0186327 A1 Aug. 25, 2005

Related U.S. Application Data

(63) Continuation-in-part of application No. 10/629,426, filed on Jul. 29, 2003.

(51) Int. Cl.
 *G01N 21/88* (2006.01)
(52) U.S. Cl. ................. 250/341.6; 250/341.1
(58) Field of Classification Search ............ 250/341.6, 250/341.1
 See application file for complete search history.

(56) References Cited

U.S. PATENT DOCUMENTS

| | | | |
|---|---|---|---|
| 3,020,745 A | 2/1962 | Sielicki | |
| 4,633,594 A | 1/1987 | Bovone | |
| 4,634,291 A | 1/1987 | Bantel et al. | |
| 4,818,118 A * | 4/1989 | Bantel et al. | ............... 374/7 |
| 4,996,426 A | 2/1991 | Cielo et al. | |
| 5,075,552 A | 12/1991 | McClelland et al. | |
| 5,091,647 A | 2/1992 | Carduner et al. | |

(Continued)

FOREIGN PATENT DOCUMENTS

| | | |
|---|---|---|
| JP | 62 198707 | 9/1987 |
| JP | 63 085438 | 4/1988 |
| JP | 01 156650 | 6/1989 |
| JP | 02 022547 | 1/1990 |
| JP | 06 341965 | 12/1994 |
| JP | 8145922 | 6/1996 |
| JP | 1096705 | 4/1998 |

OTHER PUBLICATIONS

N.P. Avdelidis, B.C. Hawtin and D.P. Almond "Transient Thermography in the Assessment of Defects of Aircrafts Composites" NDT and E International, vol. 36 Issue 6, pp. 433-439 Sep. 2003.

(Continued)

*Primary Examiner*—Albert Gagliardi
(74) *Attorney, Agent, or Firm*—Dinsmore & Shohl, LLP

(57) ABSTRACT

A system for detecting defects in paint coatings includes a temperature manipulation apparatus configured to change the temperature of a surface and a coating applied to the surface. The system may further include an infrared sensor for measuring the change in temperature (over time) of the surface and coating and a processor to compare the measured change in temperature of the surface and coating to an expected change of temperature (over time) in order to determine anomalies in the coatings. A self-referencing method of determining defects is also disclosed, wherein surrounding pixels are utilized as a reference in the detection process for calculating the change in temperature of each pixel. In addition, application of the inventive aspects to inspection of adhesion interfaces is also disclosed.

5 Claims, 21 Drawing Sheets

U.S. PATENT DOCUMENTS

| | | | |
|---|---|---|---|
| 5,111,048 | A | 5/1992 | Devitt et al. |
| 5,294,198 | A | 3/1994 | Schlagheck |
| 5,358,333 | A | 10/1994 | Schmidt et al. |
| 5,376,793 | A | 12/1994 | Lesniak |
| 5,631,465 | A | 5/1997 | Shepard |
| 5,808,303 | A | 9/1998 | Schlagheck et al. |
| 6,000,844 | A | 12/1999 | Cramer et al. |
| 6,271,878 | B1 | 8/2001 | Sera |
| 6,339,337 | B1 | 1/2002 | Matsuda et al. |
| 6,346,704 | B2 | 2/2002 | Kenway |
| 6,399,949 | B1 | 6/2002 | Roney, Jr. et al. |
| 6,400,128 | B2 | 6/2002 | Guidotti et al. |
| 6,408,917 | B1 | 6/2002 | Bett et al. |
| 6,452,180 | B1 | 9/2002 | Nistler et al. |
| 6,461,035 | B2 | 10/2002 | Meinlschmidt et al. |
| 6,491,426 | B1 | 12/2002 | Schonath et al. |
| 6,495,833 | B1 | 12/2002 | Alfano et al. |
| 6,515,284 | B1 | 2/2003 | Walle et al. |
| 6,517,238 | B2 | 2/2003 | Sun et al. |
| 2001/0042834 | A1* | 11/2001 | Kenway .................. 250/341.6 |
| 2002/0018510 | A1* | 2/2002 | Murphy et al. ............... 374/45 |
| 2002/0044679 | A1* | 4/2002 | Shepard ...................... 382/141 |

OTHER PUBLICATIONS

E. Grinzato, V. Vavilov, T. Kauppinen. "Quantative Infrared Thermography in Buildings" Energy and Buildings 29, pp. 1-9 1998.

Ch. Maierhofer, A. Brink, M. Röllig and H. Wiggenhauser "Detection of Shallow Voids in Concrete Structures with Impulse Thermography and Radar" NDT and E International, vol. 36 Issue 4, pp. 257-263, Jun. 2003.

P.J. Fito, M.D. Ortolá, R.D. De los Reyes, P. Fito and E. De los Reyes "Control of Citrus Surface Drying by Image Analysis of Infrared Thermography" Journal of Food Engineering, vol. 61 Issue 3, pp. 287-290, Feb. 2004.

Balageas D. Deom A. Boscher D., "Characterization and Nondestructive Testing of Carbon-epoxy Composites by a Pulsed Photothermal Method." Materials Evaluation, vol. 45, 1987.

D.P. Almond and S.K. Lau "Defect Sizing by Transient Thermography. I: An Analytical Treatment" *J Phys D: Appl Phys* vol. 27 pp. 1063-1069, 1994.

M.B. Saintey and D.P. Almond "Defect Sizing by Transient Thermography. II: A Numerical Treatment" *J Phys D: Appl Phys* vol. 28, pp. 2539-2546, 1995.

N.K. Del Grande and P.F. Dubrin, "Mapping Hidden Aircraft Defect with Dual Band Infrared Computed Tomography" Proc. Of SPIE V. 2455 Jun. 6-8, pp. 82-93 1992.

N.P. Avdelidis and D.P. Almond "Transient Thermography as a Through Skin Imaging Technique for Aircraft assembly: Modeling and Experimental results" Infrared Physics and Technology, vol. 45 Issue 2, pp. 103-114, Mar. 2004.

H.G. Walther "Surface Roughness Influence on Photothermal Radiometry" Applied Surface Science, vol. 193 Issue 1-4, pp. 156-166, Jun. 2002.

S. Shepard, B.A. Rubadeux and t. Ahmed "Automated Thermographic Defect Recognition and Measurement." Nondestructive Characterization of Materials IX, American Institute of Physics 1999.

Takahide Sakagami, Shiro Kubo "Applications of Pulse Heating Thermography and Lock-in Thermography to Quantative Nondestructive Evaluations" Infrared Physics and Technology vol. 43 pp. 211-218 2002.

Gary Shubinsky "Visual & Infrared Imaging for Bridge Inspection" Northwestern University BIRL Basic Industrial Research Laboratory, Jun. 1994.

Osiander R. Spicer JWM, Murphy JC. "Analysis Methods for Full-Field Time Resolved Infrared Radiometry" in Burleigh DD, Spicer JWM ed, Thermosense XVIII SPIE, Proc. 2766 pp. 218-227, 1996.

L.D. Favro, Xiaoyan Han, and R.L. Thomas "Thermal-Wave Imaging for NDE of Composites" pp. 1077-1081, Proceedings of the American Society for composites Twelfth Technical Conference: Oct. 6-8, 1998 Dearborn Inn, Dearborn Michigan.

D.J. Titman Applications of Thermography in Non-destructive Testing of Structures: NDT and E International vol. 34 pp. 149-154, 2001.

A. Wyckhuyse, X. Maldague, "Study of Wood Inspection by Infrared Thermography, Part I: Wood Pole Inspection by Infrared Thermography" Research in Nondestructive Evaluation, 13. Issue 1, pp. 1-12, Mar. 2001.

A. Wyckhuyse, X. Maldague, "Study of Wood Inspection by Infrared Thermography, Part II: Wood Pole Inspection by Infrared Thermography" Research in Nondestructive Evaluation, 13. Issue 1, Mar. 2001.

V. Vavilov, V. Demin, "Infrared Thermographic Inspection of Operating Smokestacks" Infrared Physics and Technology 43. pp. 229-232, 2002.

S. Shepard, R. Ducar. "Quantative Infrared Defect Detection in composite Aerospace Structures." 45th International SAMPE Symposium 2000.

T. Sakagami, S. Kubo, K. Sekine. "Development of a pulse heating thermographic NDT technique for detection of latent blister in corrosion protective coating on oil storage tank", Thermosense XXIII Proc, 4360, Orlando, Florida 2001.

P.G. Bison, S. Marinetti, E. Grinzato, V. Vavilov, F. Cernuschi, Dr. Robba "Inspecting thermal barrier coatings by IR thermography" Thermosense XXV, K. Elliot Cramer, Xavier P. Maldague, Editors, Proceedings of SPIE 5073 (2003).

Oslander R, Spicer JWM, Murphy JC, "Analysis methods for full field time resolved radiometry" in Burleigh DD, Spicer JWM, eds. Thermosense XVIII, SPIE Proc. 2766:218-227, 1996.

Turler D. "Predicting the geometry and location of defects in adhesive and spot welded lap joints using steady state thermographic techniques" Thermosense XXI, 3700 Orlando-Florida, pp. 54-62, Apr. 6-8, 1999.

H. Aglan, S. Shroff, Z. Abdo, T. Ahmed, L. Wang, L.D. Favro and R.L. Thomas. "Cumulative fatigue disbond of adhesive joints and its detection using thermal wave imaging" Review of progress in quantitative non-destructive evaluation. 14, p. 431-438, 1995.

D.A. Tossell "Numerical analysis of heat input effects in thermography" Journal of nondestructive testing 6 No. 2 1987.

X. Maldague, F. Galmiche, A. Ziadi "Advances in pulsed phased thermography". Infrared Physics and Technology 43,pp. 175-181, 2002.

S. Shepard, J. Lahota, B. Rubadeux, T. Ahmed "Reconstruction and enhancement of active thermographic image sequences" Optical Engineering 42 (5) pp. 1337-1342, May 2003.

X. Maldague, J. Cote, D. Poussart, V. Valvilov "Thermal Tomography for NDT of industrial materials" Canadian Society of Nondestructive Testing Journal pp. 22-32, May-Jun. 1992.

Vavilov V. "Dynamic Thermal Tomography: Perspective Field of Thermal NDT" in Semanovich SA, ed. Thermosense XI, SPIE Proceedings, 1313. Pp. 178-182, 1990.

L.D. Favro, T. Ahmed, Xianyan Han, L. Wang and S. M. Shepard "Thermal Wave Imaging of Aircraft Structures" Review of Progress in Quantitative Non-destructive Evaluation, 14, pp. 461-466, 1995.

V. Vavilov, X. Maldague "Dynamic Thermal Tomography: New Promise in the IR Thermography of Solids" SPIE vol. 1682, Thermosense XIV, pp. 194-206.

L.D. Favro, X. Han, P.K. Kuo, R.L. Thomas "Measuring defect depths by thermal-wave imaging" SPIE vol. 2766, pp. 236-239.

X. Maldague "Theory and Practice of Infrared Technolgy for Nondestructive Testing" Wiley Interscience Publication, Chapters 1,6,11. 2001.

Feeler, Robert A., "Infrared Thermography Offers New Possibilities for Nondestructive Testing," Flight Safety Foundation, Aviation Mechanics Bulletin, May-Jun. 1995.

Shubinsky, Gary, "Visual & Infrared Imaging for Bridge Inspection," Northwestern University BIRL Basic Industrial Research Laboratory, Jun. 1994.

"Heat Conduction in Solids with Buried Discontinuities," Nondestructive Testing Handbook, Infrared and Thermal Testing, Third Edition, vol. 3, p. 62.

Favro, L.D., Xiaoyan Han, P.K. Kuo and R.L. Thomas, "Measuring Defect Depths by Thermal-Wave Imaging," Thermosense XVIII: An International Conference on Thermal Sensing and Imaging Diagnostic Applications, vol. 2766, pp. 236-239, Mar. 1996.

Maldague, Xavier P.V., "Theory and Practice of Infrared Technology for Nondestructive Testing," May 2001.

* cited by examiner

SYSTEMS AND METHODS FOR INSPECTING COATINGS, SURFACES AND INTERFACES

CROSS REFERENCE TO RELATED APPLICATION

This application is a continuation-in-part of prior copending U.S. application Ser. No. 10/629,426 filed Jul. 29, 2003, the entire disclosure of which is hereby incorporated by reference herein.

FIELD OF THE INVENTION

This invention relates to systems and methods for detecting defects in surfaces and to coatings applied to substrates. More particularly, this invention relates to systems and methods for detecting surface and subsurface defects in vehicle paint coatings, surfaces, and interfaces using an infrared camera.

BACKGROUND OF THE INVENTION

One of the most important methods in high quality automobile and other vehicle or machine production involves the inspection of the exterior appearance (i.e. the quality of the paint finish on a part). Usually, an automobile shell, for example, receives at least four coatings including a protective coat, an adhesion aid coat, a paint coat and a clear coat. Defects occurring in the coating method of a properly prepared surface that may diminish the perceived quality of the exterior paint include, but are not limited to, dust, hair, metallic particles, over spray, incomplete spray, stripping and flake penetration. Inspection for such defects will ensure the exterior quality of the product from the customer's point of view.

Previously, evaluation of the quality of the paint finish was often based on human inspection, which can be a tedious and subjective method and one that requires meaningful skill and training. Other inspection procedures have been based on the use of charge-coupled device (CCD) optical sensors that sense imperfections through light reflected off of the finished surface. However, this technique is not particularly effective for complex, curved and/or hidden geometries (i.e. automobile bodies) because of its sensitivity and dependence on reflection and scattering angles.

In addition, it has been generally known to use infrared cameras to inspect certain products (i.e. semiconductor chips) for surface anomalies or defects. However, such inspection techniques are based solely on the spatial analysis of pixel values with that of known (standard) values without any account for the temporal behavior of the pixel values (e.g., change of temperature over time).

In addition, while other techniques have been utilized to measure the change of temperature over time, such techniques do not compare measured change of temperature of pixels of the same data file to that of surrounding pixels, and therefore fail to efficiently and effectively detect subsurface anomalies. Moreover, many inspection procedures require the need for a known non-defective area within a thermal profile for thermal deviation determinations, and others require continuous acquisition of a sequence of data files. Such procedures can also require operator intervention, significant time requirements, and/or computational complexities not suited for realtime applications.

As such, there is a desire for improved systems and methods capable of inspecting not only surface, but subsurface anomalies in multi-layered paint coatings, and in other related surfaces.

SUMMARY OF THE INVENTION

Accordingly, the present invention is intended to address and obviate problems and shortcomings and otherwise improve previous systems and methods for inspecting coatings on surfaces, and particularly for automotive paints and coatings, bonded joints and other surfaces. According to some aspects, techniques are provided for more efficiently detecting subsurface anomalies. In accordance with other aspects, techniques are provided for realtime applications, and for minimizing need for operator involvement.

To achieve the foregoing and other objects and in accordance with the exemplary embodiments of the present invention, a system for detecting defects in coatings comprises a temperature manipulation apparatus configured to change the temperature of the surface and the coating, an infrared sensor configured to measure the change in temperature of the surface and the coating over time and a processor configured to compare the measured change in temperature of the surface and the coating over time to an expected change of temperature over time.

To still further achieve the foregoing and other objects of the present invention, a system and method for detecting defects in coatings comprises the steps of measuring a thermal profile of a surface to create a thermal signature, applying a first coating to the surface, changing the temperature of the coated surface, taking a first measurement of emitted radiation from the coated surface and comparing the emitted radiation to the thermal signature. The method also comprises the steps of applying a second coating to the coated surface, changing the temperature of the coated surface, taking a second measurement of emitted radiation from the coated surface and comparing the first measurement to the second measurement.

To yet further achieve the foregoing and other objects in accordance with other exemplary embodiments of the present invention, a system and method for detecting defects in coatings comprises the steps of applying a plurality of coatings to a surface, configuring an expected change of temperature, manipulating the temperature of the coated surface, measuring the change of temperature in the normally manipulated coated surface and comparing the measured change of temperature in the manipulated surface to the expected change of temperature.

To even further achieve the foregoing and other objects in accordance with additional exemplary embodiments of the present invention, a system and method for detecting defects in coatings comprises the steps of measuring a thermal profile of a surface to create a thermal signature, applying a first coating to the surface, and changing the temperature of the coated surface. The method further includes the steps of taking a first measurement of amount of emitted radiation from the coated surface, comparing the emitted radiation to the thermal signature, applying a second coating to the first coating, changing the temperature of the coated surface, taking a second measurement of amount of emitted radiation from this coated surface and measuring change in temperature thereof. The method also includes the steps of configuring an expected change of temperature, comparing the first measurement to the second measurement and comparing the measured change in temperature of the coated surface to the expected change of temperature.

Still other embodiments, combinations, advantages and objects of the present invention will become apparent to those skilled in the art from the following descriptions wherein there are shown and described alternative exemplary embodiments of this invention for illustration purposes. As will be realized, the invention is capable of other different aspects, objects and embodiments all without departing from the scope of the invention. Accordingly, the drawings, objects, and description should be regarded as illustrative and exemplary in nature only and not as restrictive.

BRIEF DESCRIPTION OF THE DRAWINGS

While the specification concludes with claims particularly pointing out and distinctly claiming the present invention, it is believed that the same will be better understood from the following description taken in conjunction with the accompanying drawings in which:

DETAILED DESCRIPTION OF EXEMPLARY EMBODIMENTS

Figure 1:
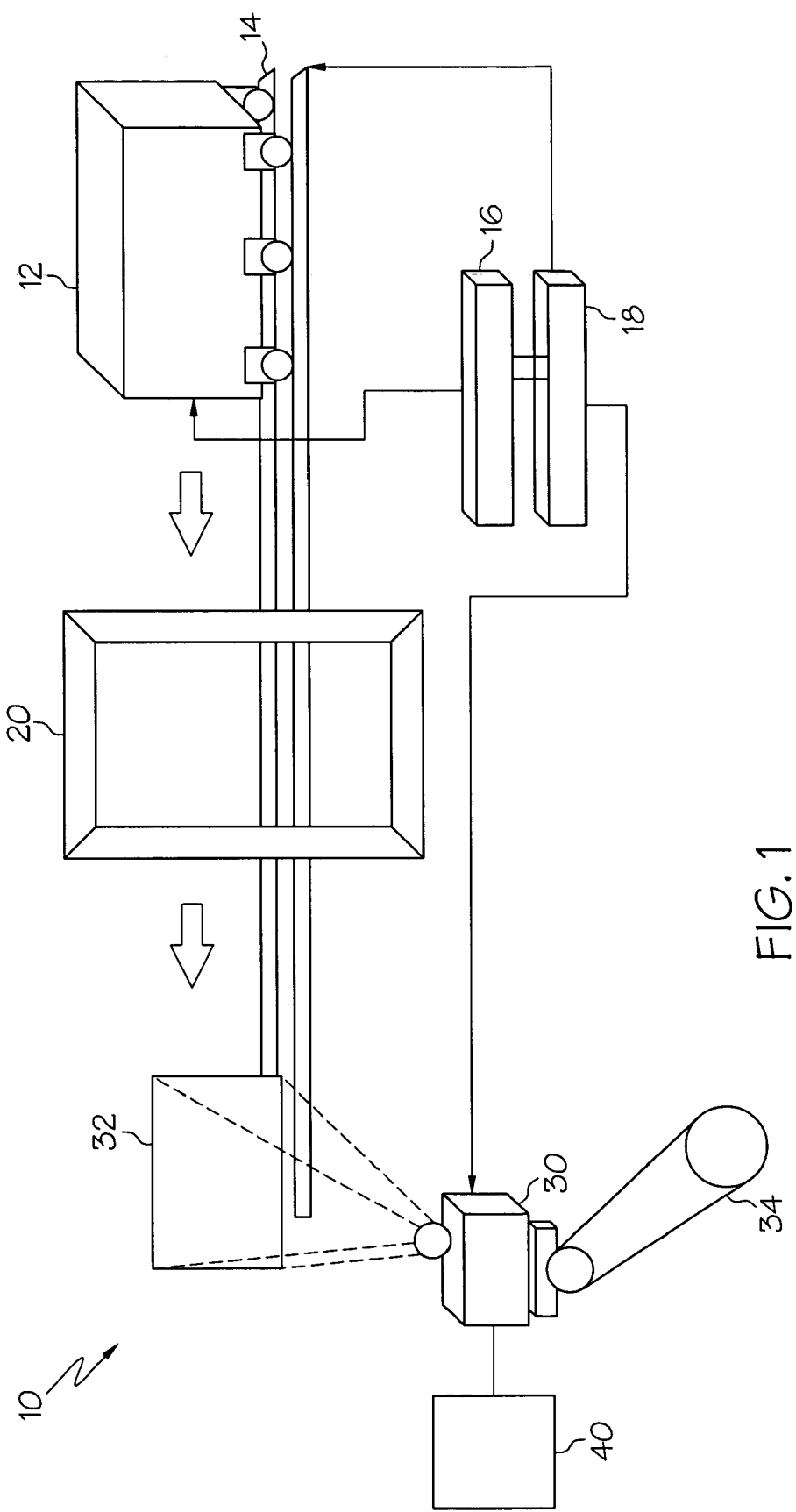
FIG. 1 is a schematic view of an exemplary system and method for creating a thermal signature in accordance with the present invention.

One principle of defect detection utilized in embodiments herein relates to thermal mismatch. In particular, when the temperature of a surface and/or coating(s) bearing such defects is manipulated and viewed by an infrared sensor, the defects will be effectively magnified and distinguishable as spots of different thermal imprint or color. More particularly, the thermal characteristics or effusivity difference between the defect and the surrounding paint or surface creates a thermal mismatch. The thermal mismatch results in a different thermal wave reflection from the defect as compared with its surroundings. The concept of thermal mismatch may be represented by the formula:

$$\Gamma = \frac{\sqrt{k_1 p_1 c_1} - \sqrt{k_0 p_0 c_0}}{\sqrt{k_1 p_1 c_1} + \sqrt{k_0 p_0 c_0}}$$

wherein k=thermal conductivity, p=density and c=specific heat. Sub 1 indicates properties of the defect whereas sub 0 indicates properties of the surroundings.

Because effusivity $e=\sqrt{k \cdot p \cdot c}$, then:

$$\Gamma = \frac{e_1 - e_o}{e_1 + e_o}$$

Accordingly, thermal mismatch is the difference between the thermal properties or characteristics (effusivity) of the defect and its surroundings as sensed by the sensing mechanism (e.g., the infrared camera or sensor, as will be discussed further below). For example, in determining the thermal mismatch between an air pocket and resin epoxy, wherein the air pocket (defect) has a known thermal effusivity of 9.19 W. $(\text{sec}.m^{-2}.K^{-1})^{0.5}$ and the epoxy resin (surroundings) has a known thermal effusivity of 667 W. $(\text{sec}.m^{-2}.K^{-1})^{0.5}$ $$\Gamma(\text{thermal mismatch}) = \frac{e_1 - e_o}{e_1 + e_o} = \frac{9.19 - 667}{9.19 + 667} \approx -0.97$$

Accordingly, in this example, only approximately 97% of the thermal wave will reflect from the air pocket interface as compared with the epoxy resin, thereby causing a deviation in the temperature profile between the air pocket and the epoxy resin at that particular spot.

As a result of the thermal mismatch between the defect and its surroundings, thermal change or contrast profiles, which are parameters that account for the speed of the change in temperature of the defect as compared to the speed of change of its surroundings, can be established. More particularly, because the different effusivity values of the defects result in a different rate of cooling ΔT compared with its surroundings, the contrast between the defect and its surroundings can be observed. The concept of thermal contrast or thermal change ($T_c$) may be represented by the formula:

$$T_c = \frac{T_d(t) - T_d(t_0)}{T_s(t) - T_s(t_0)}$$

wherein T=temperature, t=time, d=defective spot, $t_0$ is the initial time, and s=non-defective spot. Accordingly, thermal contrast is the deviation in the measured temperature profile ΔT for various data points or pixels of the surface as compared to the normal (expected) profile (i.e., an expected temperature change over time for the points), due to the existence of a foreign material or excess or absence of coating material(s) (e.g., defect).

Applying these principles, the systems and methods of the present invention, in one or more of the embodiments, are capable of detecting defects in single and multi-layered coatings by measuring emitted radiation and comparing that measurement to 1) a known, expected, or model thermal profile; and/or 2) a previously measured thermal profile, such as of a shell and/or previous layer; and/or to 3) determine a thermal contrast or change based upon the measurement and compare that value to an expected contrast or change. At least some embodiments of the invention allow for identification of a defect in a two-dimensional plane as well as a particular depth or thickness of the defect.

Referring to the drawing figures in detail, wherein like numerals indicate the same elements throughout the drawing figures, FIG. 1 illustrates at least part of an exemplary system 10 for viewing and determining a thermal profile. The exemplary system of FIG. 1 may be applied to a situation where a surface, herein referred to as a shell or workpiece 12, is raw (e.g. does not have a coating) and a thermal profile of the shell (i.e., the uncoated part or the uncoated part with a layer of primer) may be measured to create a shell thermal signature for later comparison to the thermal profile of the same shell with one or more additional coatings (described later herein). Of course, shell 12 could comprise a complete vehicle body, portions of a vehicle, or a single piece to be coated. Alternatively, the exemplary system of FIG. 1 may also be applied to a situation wherein shell 12 comprises one or more coatings and the thermal profile of the shell and coatings is sought to be measured to check for defects. For purposes of this example, however, it is assumed that shell 12 is raw and/or that the coatings of interest have yet to be applied.

As illustrated in FIG. 1, the exemplary system 10 may comprise a temperature manipulation apparatus 20, a sensing mechanism such as an infrared (IR) sensor 30, and a processor 40. In this example, temperature manipulation apparatus 20 is illustrated as comprising a curing oven. Curing ovens are often used in the industry to "bake" a coating or layer of paint to the surface of an automobile shell. In the present invention, not only does the curing oven function to "bake" coatings and/or paint onto the shell 12, but also provides appropriate temperature manipulation of the shell and coatings so that emitted radiation and change of temperature may be optimally measured by IR sensor 30 (discussed later herein). As known in the industry, such a curing station or oven can comprise a plurality of heater banks and/or other elements to raise the temperature of the shell, its surfaces to be coated and/or the coating(s) applied as appropriate. In an exemplary embodiment for applying paint and/or other surface coatings to automobile panels or the like, the temperature of the curing oven may be set in the range of 150–250° C. This range has been found to be particularly effective to ensure proper "baking" of a coating while manipulating the temperature of the shell (and coatings) so that a desired thermal profile can be measured.

In another embodiment, however, curing oven 20 may be set at any desired temperature to adequately "bake" or cure a coating and/or provide optimal conditions to measure a thermal profile. In addition, it should be understood that because the present invention is directed toward detecting defects through measurements of emitted radiation and change of temperature during any heat transition, the temperature manipulation apparatus may also include any combination of heating and/or cooling devices used to manipulate the temperature test surface (and coatings) to provide optimal measurement of a thermal profile. In this regard, it should be understood that the "manipulation" contemplated can comprise increasing or decreasing relative temperatures. Such combinations include, but are not limited to application of a coating at a different temperature than the shell surface to create a measurable temperature differentiation therebetween and/or measuring the thermal profile of the shell 12 while the subject surface is being heated. Such combinations may further include use of sound waves or ultrasound waves that are converted to thermal energy inside the material and then detected by the IR sensor or other appropriate sensing mechanism.

Once the temperature of the shell 12 is manipulated in the curing oven 20, shell 12 may be inspected by IR sensor 30. As illustrated in FIG. 1, IR sensor 30 may be configured with a predetermined field of view 32 for inspecting shell 12. IR sensor 30 may be appropriately positioned to inspect shell 12 as the result of input from shell recognition sensor 16 and belt speed sensor 18. For example, shell recognition sensor 16 may be integrated, or configured to communicate with the IR sensor 30 and/or processor 40 for determining the type of shell or workpiece entering the curing oven 20. The recognition of the shell may be useful to assure that the IR Sensor 30 is calibrated and situated to capture an appropriate field of view 32 (e.g. size or angle) for the specific shell 12. In addition, belt speed sensor 18 may be integrated with the IR Sensor 30 and/or processor 40 for determining the speed of the belt 14 so that the IR Sensor may be synchronized or matched to position itself at a starting position appropriately and move around shell 12 on robotic arm 34. Also, IR sensor may be stationary and situated to take snap shots (e.g., plan or side views). In another embodiment, any combination of sensors and/or logic may be integrated with IR sensor 30 so as to properly position one or more IR sensors 30 to measure the desired field of view 32.

Still referring to FIG. 1, a delay between the time that shell 12 exits the curing oven 20 and is measured by the IR sensor 30 may be desired for multiple reasons. For example, it is believed that at the time when shell 12 first exits curing oven 20, shell 12 may still be absorbing heat, and therefore, may provide a varying emission of radiation for measuring the thermal profile. Accordingly, it is believed that it may be desirable to take measurements at some point during the cooling (i.e., after maximum temperature achieved) of the shell and/or coating(s) depending on the shell type and composition, and any associated coatings. As previously discussed, however, the present invention contemplates the use of any combination of heating and cooling to provide a temperature at which optimal radiation is emitted for measurement.

In addition, a delay between the curing oven 20 and measurement by the IR sensor may be desired in accordance with a calculated maximum contrast for the shell 12. More particularly, it is believed that as a result of the different thermal properties among various shells and/or layered coatings bearing defects, an optimal time window will generally exist for viewing a maximum thermal contrast (e.g. $\Delta T$, the deviation in the measured temperature profile and the normal or expected profile due to the existence of a foreign material). For example, when a workpiece or shell has cooled to near room temperature, less thermal contrast will generally be detectible, and as a result sensitivity or accuracy of the defect detection will be reduced. As discussed later herein, by measuring the shell 12 during its particular window of thermal maximum contrast, focus may be given to the depth of a potential defect in one or more layers of a multi-layered coating.

IR sensor 30 may comprise any sensor or sensing arrangement configured to at least measure radiation emitted from a surface and/or the change of temperature of a surface over a period of time. For example, IR sensor 30 of the above example may be a TVS 8500 manufactured by CMC Electronics which is capable of achieving excellent observation ranges for the present invention of about 3 to 5 µm (Wavelength) at a temperature range of <40° C. over ambient temperature. While such observation ranges are currently believed to be particularly applicable for automotive coatings which have relatively low curing temperatures of about 200° C. or less, other observation ranges are contemplated by the present invention.

IR sensor 30 may change the field of view 32 through manual and/or automatic focusing of its lenses or by positioning itself at a proper location relative to shell 12 such as through appropriate positioning of robotic arm 34. Accordingly, while it is contemplated that only one IR sensor 30 might be needed to capture all desired fields of view 32, it should be understood that any number of IR sensors may be used to together to capture any number of fields of view. In such embodiment, IR sensors may be temporarily synchronized to compare temperature contrasts at same time.

As illustrated in FIG. 1, IR sensor 30 can measure an initial or base emitted radiation (a thermal profile) from the raw shell 12 by establishing an appropriate field of view 32. As discussed later herein, IR sensor 30 may map an area under a field of view into a grid, wherein each square or pixel of the grid may reflect a desired area to measure. If the raw shell is acceptable (e.g. does not comprise fatal defects such as cracks, dents, etc. that may prevent subsequent acceptable coating), a thermal profile for the shell (its thermal signature) may be created.

The thermal signature of the shell 12 may be stored in processor 40 or elsewhere for access by processor 40. Processor 40 may include, for example, any memory or computer configured to log data and perform comparison and analysis of data recorded. The shell thermal signature may be used as a template to be later compared with the thermal profile of the shell having one or more coatings, for detection of defects. More particularly, because the shell thermal signature may provide a template (i.e. a map of any preexisting acceptable flaws or defects), defects detected upon comparison to a thermal profile taken of the shell 12 with one or more coatings can be distinguished from the flaws/defects already known to be existing on the shell.

Another unique feature of this system and method is that multiple shell thermal signatures for a variety of shells may be created and stored within processor 40 (or so that processor 40 has access to them). For example, recognition sensor 16 may sense the geometries of the shell and transmit signals regarding the geometries to processor 40 to discover whether an applicable thermal signature or one for a similar model has been created. If so, shell may be diverted directly to Paint Station I 60, described below. Alternatively, if processor 40 does not recognize shell 12, shell 12 may be directed through system 10 to create a thermal signature. In another embodiment, shell 12 may include an identification tag or other identifying apparatus configured to transmit signals to the IR sensor or processor regarding shell type. Because the system of the invention is capable of establishing a distinct thermal signature for each shell, different shell models may follow each other along beltline 14.

Figure 2:
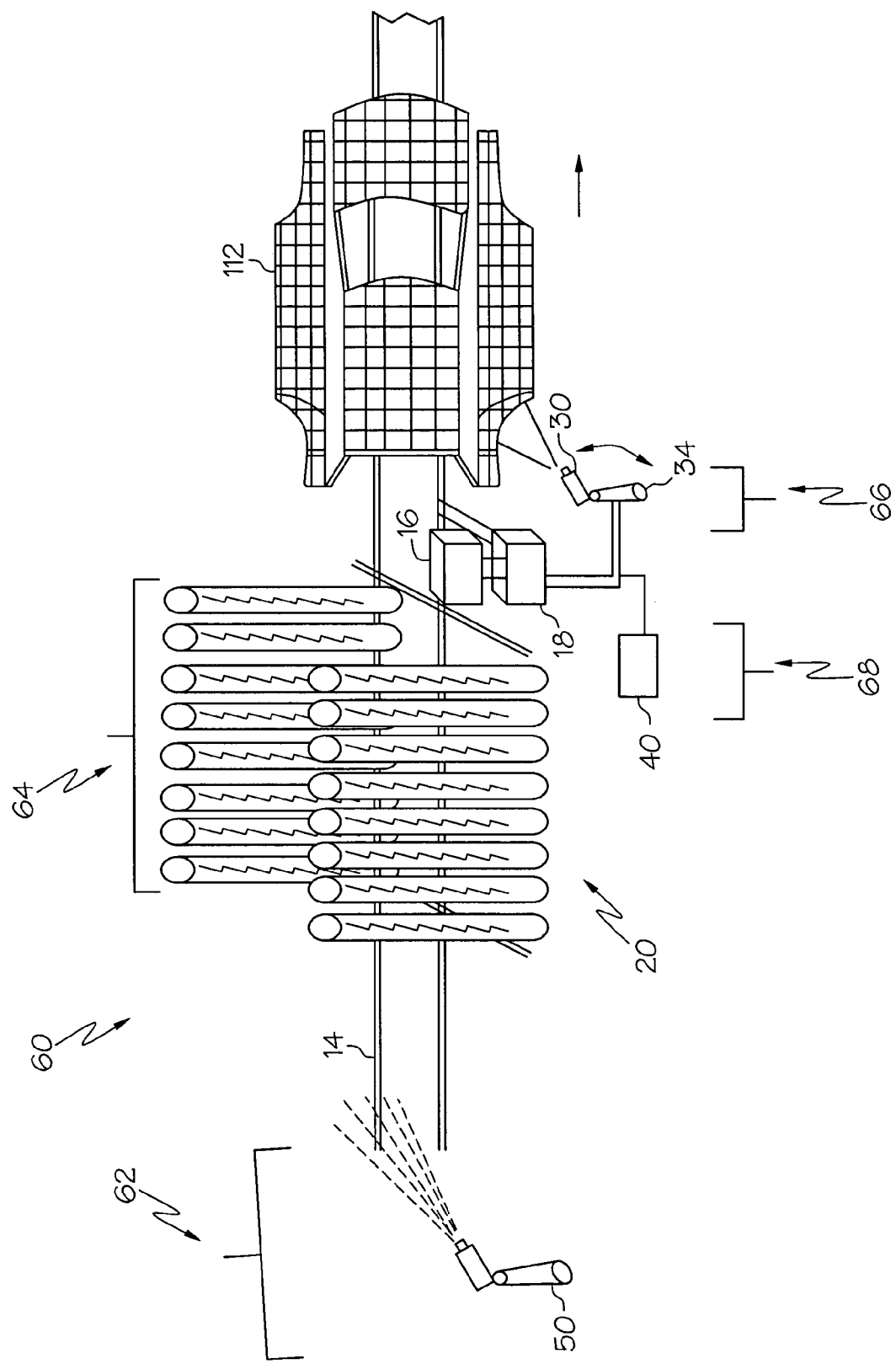
FIG. 2 is a schematic view of an exemplary station in a system and method for coating a surface and measuring a thermal profile in accordance with the present invention.

Once a shell thermal signature has been created and stored for a particular shell 12, the shell may be moved to a first coating station. Referring to FIG. 2, a first coating station is illustrated as Paint Station I 60. For purposes of this example, the exemplary system illustrated in FIG. 2 comprises similar components as that of FIG. 1 with the addition of application apparatus 50. As later discussed herein, an exemplary coating station, such as Paint Station I, may be configured to measure not only the thermal profile of shell 12 with one or more coatings, but also the change in temperature of shell 12 and any associated coatings after temperature manipulation.

Paint Station I 60 is illustrated as comprising a coating application apparatus 50, a temperature manipulation apparatus 20, an infrared sensor 30 and a processor 40. As illustrated in FIG. 2, application apparatus 50 may comprise a paint gun or electrostatic spraying device as generally known in the industry configured to apply paint or another desired coating to a surface such as automobile shells. In another embodiment, any apparatus configured to apply paint and/or any other coating to a surface may be used.

Similar to FIG. 1, temperature manipulation apparatus 20 may comprise a curing oven configured to heat the shell and first coating 112 from application apparatus 50. As previously discussed, temperature manipulation apparatus 20 may also comprise any combination of heating and/or cooling elements or apparatuses configured to manipulate the temperature of the shell and/or coating 112. Such elements might include heat lamps, infrared heating elements, convection areas, microwave heaters or the like. As illustrated in FIG. 2, car recognition 16 and belt speed 18 sensors may be positioned on the opposite end of curing oven 20 to sense the shell 112 and belt speed once the shell 112 has exited the curing oven 12. As also to be understood, bar code readers, optical sensors, contact switches or other identification equipment and/or alignment arrangements can also be utilized to properly queue a shell 112 for IR sensing. As discussed above, such sensors may be used to appropriately position IR sensor 30 to capture an appropriate field of view.

The systems described above and illustrated in FIGS. 1 and 2 can be used, for example, to inspect automobile shells only and automobile shells with coatings applied thereto for defects that may deteriorate the exterior appearance of the automobile. Moreover, the present invention contemplates multiple methods of inspecting automobile coatings utilizing the systems set forth above. For example, one method of inspecting a multi-layered coating for defects includes analysis of each successive layer of coating with comparison to a previous layer. More specifically, the thermal profile for a coating may be compared with the thermal profile measured from a previous coating to determine the existence of a new or unresolved defect. Accordingly, a number of coating and inspection stations, similar to Paint Station I, may be linked together to create a complete coating line wherein each of the coating stations is configured to communicate data regarding previous coating stations, as well as statistical method data throughout the coating line.

Figure 3:
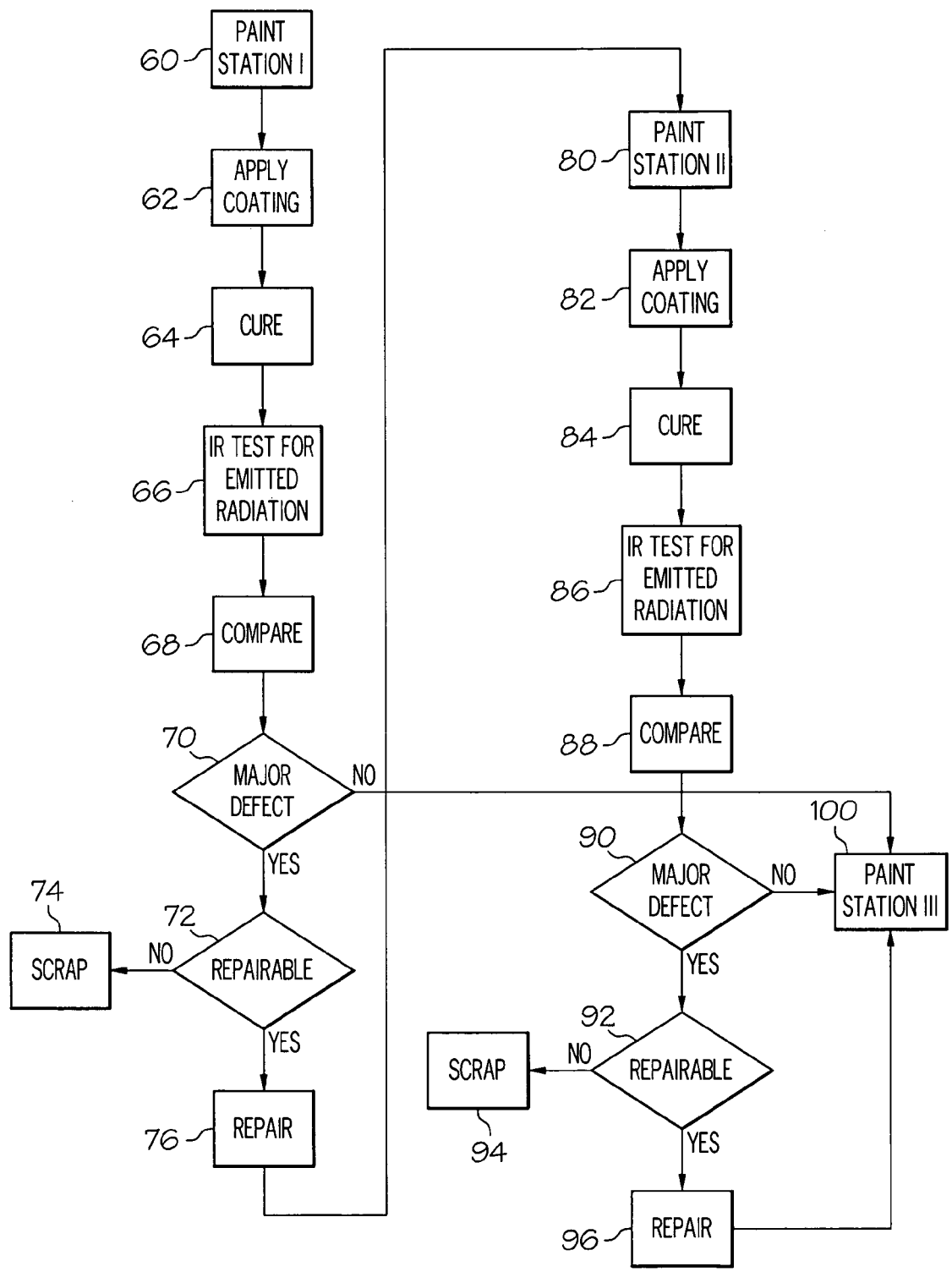
FIG. 3 is a simplified flow chart illustrating exemplary steps in a method of inspecting coatings in accordance with the present invention.

Referring to FIG. 3, exemplary steps for a method for inspecting a multi-layered coating for defects is illustrated. For purposes of this example, it is assumed that a shell thermal signature for the raw shell (e.g. 12 in FIG. 1) has been created or is otherwise known. Referring to FIGS. 1–3, raw shell 12 progresses to Paint Station I 60 for coating. Once the coating is applied 62, the shell (112 in FIG. 2) may be moved to temperature manipulation apparatus 20 (e.g. curing oven). The surface and coating may be manipulated by curing oven for curing and pre-testing manipulation (step 64).

After an appropriate amount of time, IR sensor 30 may take appropriate field of view pictures to measure the radiation emitted from the shell and the coating (shown at step 66). Accordingly, a thermal profile or "picture" refers to the capture of a single thermal image at an instant in time (t). In taking a picture of the thermal profile, the IR sensor 30 may map an area under a field of view into a grid (i.e. FIG. 2), wherein each square or pixel of the grid may reflect a desired area to measure. For example, the grid may be divided up into land areas of 0.1 mm. Such land area may be based, for example, on the size of a defect normally visible to a casual naked eye, or the smallest size defect which may be practically repairable.

The IR sensor may transmit the measured thermal profile to a processor (e.g. 40), wherein the processor may compare (step 68) the profile with the shell thermal signature of the automobile shell. In this stage (68) of the method (e.g. Paint Station I), the profile captured by IR sensor is compared with the shell thermal signature created from the raw shell (12 in FIG. 1). More particularly, the grid of the thermal profile viewed and captured by the IR sensor may be electronically overlaid onto the grid of the shell thermal signature. Deviations between the thermal profile and the thermal signature may be indicated electronically within the processor or visually on a monitor (not shown) by spots of varying color thereby indicating the presence of a defect.

Upon subsequent coatings, as discussed below, the thermal profile of shell and coatings may be compared to a previous thermal profile measured from a shell and fewer coatings taken at a previous instance in time, similarly at stage 68. In another embodiment, not only may the captured profile be compared with the shell thermal signature, but it can also be compared to an acceptable preexisting model profile stored within the processor. More particularly, through manual inspection or accumulated data from previous inspections, a model profile (or "standard") indicating a surface coating (and/or ranges of deviations) of acceptable quality may be created and stored within the processor. The model profile can be formed based on thermal modeling (temperature rise profiles) discussed herein with real-life repeated measurements of this emission difference. The idea behind acquiring first and second coating layer thermal emissions and comparing the difference to a model profile is to monitor coat layers build up (i.e. thickness) and integrity (i.e. existence of foreign contaminants).

A deviation from a model profile indicates a defective behavior in the coat layer that may be related to (1) coverage of coat layer two over layer one; (2) thickness of coat layer two; (3) defective interfacing between coat layer one and two; and/or (4) existence of foreign contaminants in coat layer two. Accordingly, the thermal profile captured by the IR sensor may be additionally compared to this acceptable model profile for detection of deviations and insuring quality control set to a predetermined standard.

If a defect is indicated upon comparison, the processor may determine (at step 70), based on programmed acceptable standards, whether the defect is of such a nature that it may create a problem for subsequent coatings and/or will result in an unsatisfactory final product (major defect). Where there is a major defect, the processor may then determine at step 72, again based on programmed acceptable standards, whether the defect is repairable by comparing defect parameters with stored data of historic defect phenomenon. If the defect is not repairable, in one embodiment, the shell may be sent for scrap at step 74. If it is determined that the surface and coating is repairable 76, a technician may either repair the defect on the spot, direct the shell to a repair "queue" for handling, or repair the defect later in the coating method (as it may be possible to repair the defect by simply applying the next coat). If repaired, the shell might be re-inserted to the finish method, such as in line for Paint Station II at step 80.

If the processor determines that no major defects are indicated, the automobile shell may pass to Paint Station II (step 80). Similar to Paint Station I, Paint Station II may apply a coating (step 82), transfer shell to curing oven (step 84) and measure the thermal profile of the shell, first coating and second coating (step 86). The IR sensor may transmit the thermal profile to the processor for comparison at step 88. At this stage the processor may compare the thermal profile measured at Paint Station II to the thermal profile measured at Paint Station I for deviations. Deviations among the thermal profiles may indicate defects in the newly applied coating (e.g. coating applied at Paint Station II). In addition, processor may also compare the thermal profile measured at Paint Station II to the shell thermal signature of the shell or a preexisting model profile (or standard) for an acceptable shell with two coatings in order to further check for defects.

If a major defect is detected as described above, the processor may determine at step 92 whether to send the shell to scrap (step 94) or repair (step 96). If no major defects are indicated, the automobile shell may move to Paint Station III 100 to follow steps similar to steps 80–86 discussed above. The thermal profile measured at Paint Station III, however, can be compared to the thermal profile measured at Paint Stations I and/or II for deviations. In addition, the thermal profile measured at Paint Station III may be compared to the thermal signature of the shell or a preexisting model profile (or standard) for an acceptable shell with three coatings.

Accordingly, in this exemplary method of the present invention, because thermal profiles of each individual coating can be measured and compared not only to previous thermal profiles, but also to the thermal signature of the automobile shell and an acceptable preexisting model profile, defects can be more accurately detected and localized by layer. This detection method may be particularly useful in applications where, despite detection of major defects, the coating method is allowed to continue to or toward completion. In this situation, data regarding each coating layer and detected defects may be compiled so that the defects may be localized and more appropriately repaired as needed at the end of the coating method, rather that at each coating stage. For example, a defect in the top coat might only require a light repair procedure on the topcoat and clear coat, while another defect in the primer layer may need more robust activities.

In some applications, it may be desired to take a single measurement sometime later in the method, or at the completion of the coating method, rather than measuring the thermal profile of each coating. Defect detection of this type would enable a method whereby not only surface defects could be indicated as described above, but also subsurface defects. As such, another aspect of the present invention includes a method for detection and localization of subsurface defects at any point in the coating method, including completion, by taking successive measurements (e.g. thermal profiles or thermal pictures of the field of view) to determine the change in temperature (e.g. thermal contrast) between a defect and its surroundings. In another embodiment, IR sensor may scan the field of view over an interval of time. The measurement in the change of temperature may be compared to an expected change in temperature (e.g. expected thermal contrast) configured from a known thermal emissivity of the particular defect and its surroundings. This method can not only detect a surface defect located in the outermost coating of the paint, but may also detect and localize a defect in any one or more of the coating layers beneath the outermost coating.

Figure 4:
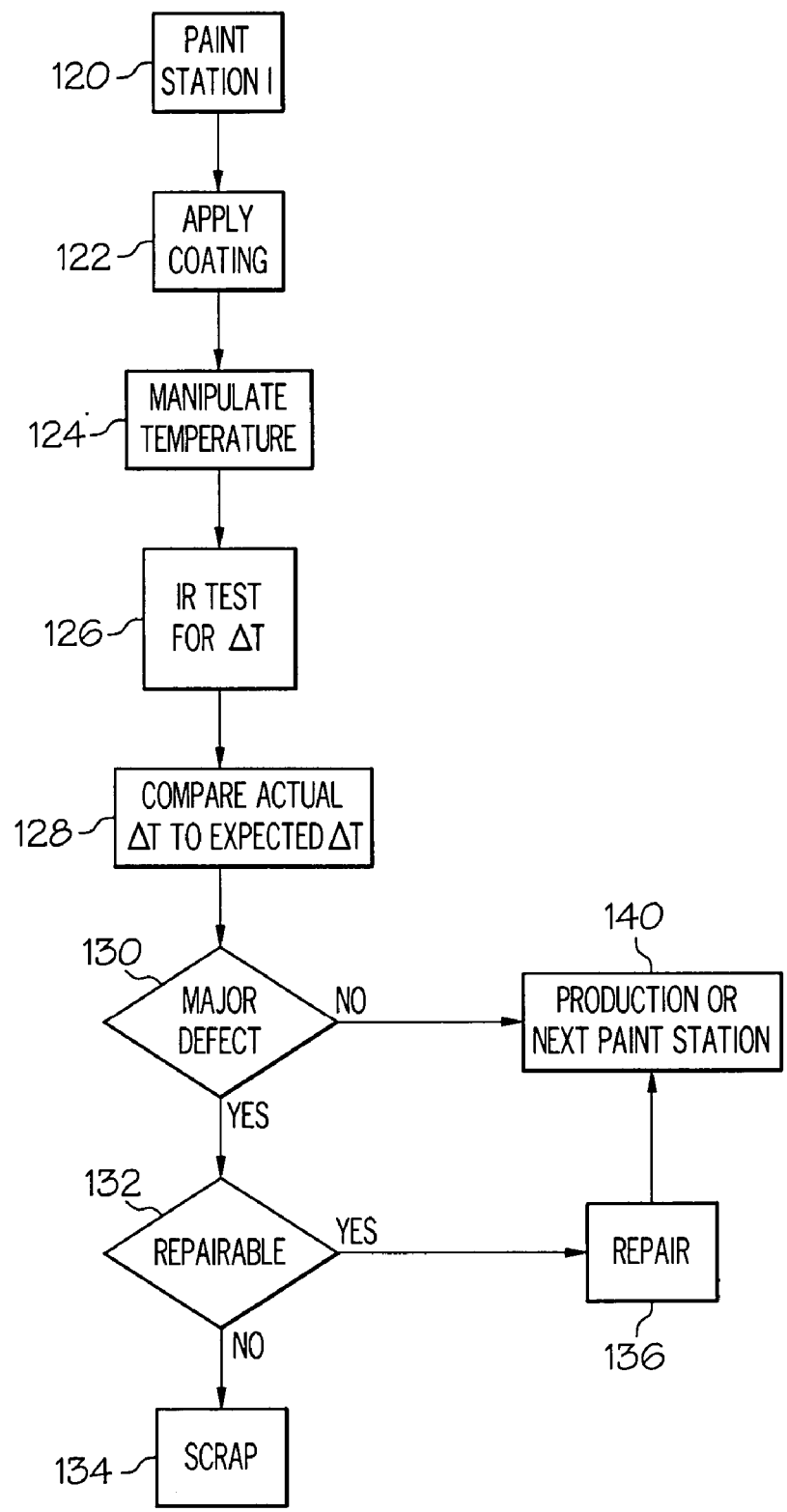
FIG. 4 is a simplified flow chart illustrating exemplary steps in an alternate embodiment of the method of inspecting coatings in accordance with the present invention.

For example, referring to FIG. 4, an alternative method for detecting and localizing surface and subsurface defects is illustrated. As previously discussed, the principle of this aspect of the inventive method is to measure the changes in temperature of the shell and coatings once heated up in a temperature manipulation apparatus (i.e., curing oven). As illustrated in FIG. 4, a coating may be applied at step 122 to the automobile surface. Once the coating has been applied, the temperature of the automobile shell and coatings may be manipulated 124 as discussed above. Once the coated shell is up to temperature and heating ceases, an IR sensor may measure (at step 126) the speed of the change of temperature of the shell and defects within the coatings at a time when maximum contrast between the defects and their surroundings is achieved. As previously discussed, the thermal effusivity difference between the defect and the surrounding coatings creates a thermal mismatch. The thermal mismatch results in a different thermal wave reflection from the defect as compared with its surroundings, and, as a result, thermal contrast profiles can be established by the IR sensor. Maximum thermal contrast may vary among shells and associated coatings, and timing and specific procedures for measuring the temperatures and changes can be varied accordingly.

The IR sensor may transmit the thermal contrast/change data to the processor, which may be programmed with known thermal effusivity values for the coatings and defects, and ultimately, expected change of temperature. For example, because a coating and defect may have a known thermal conductivity, density and a specific heat capacitance, an expected change of temperature (how quickly the shell, coatings and defects should change temperature) can be determined. Accordingly, the actual change in temperature from the cooling shell, coatings and defects and the thermal contrast therebetween may be compared to an expected change in temperature to determine the presence of any defects. Similarly, actual change in temperature of detected defects may be compared to programmed data and data accumulated through previous tests to determine the specific type and severity of the defect (i.e., dust, hair, metal flakes, etc.) at stage 130. If no major defect is indicated, then the automobile shell may move to Production or to the next Paint Station (step 140).

To form an expected change of temperature or expected thermal contrast for a coating, as discussed above, thermal properties (i.e. $\kappa$, $\rho$, c) can be identified, wherein:

$$\text{effusivity } e = \sqrt{\kappa \cdot \rho \cdot c} \text{ and diffusivity } \alpha = \frac{\kappa}{\rho \cdot c}$$

The thermal effusivity value determines the thermal inertia of the coating. Applying this inertia and diffusivity values into the following heat evolution (for heating temperature manipulation) conduction equation provides a temperature rise profile (surface temperature rise upon heating):

$$T(t) = C_c \cdot \sqrt{t} \left[ 1 + \sum_{n=1}^{\infty} -2 \cdot \Gamma^n \cdot \left\{ \exp\left(\frac{-n^2 L^2}{\alpha_o t}\right) - \frac{nL\sqrt{\pi}}{\sqrt{\alpha_o t}} \operatorname{erfc}\left(\frac{nL}{\sqrt{\alpha_o t}}\right) \right\} \right]$$

wherein t is the time variable, $C_c$ is a constant related to the heat absorption, L is the thickness of coat layer. As such, monitoring thermal emission of a coating under inspection to set practical tolerances and modifications on its temperature rise profile leads to the formation of an expected change in temperature (e.g. expected thermal contrast).

Based on the comparisons discussed herein, where a major defect is observed, the defect may be localized to a specific area at stage 130. As mentioned, IR sensor may map an area under a field of view into a grid, wherein each square or pixel of the grid may reflect a desired area to measure. Processor can compare the speed of the change of temperature of relative adjacent pixels to one another to determine, based on expected change of temperature (discussed above), the location of anomalies (defects). According to one aspect, comparison of adjacent pixels can be carried out according to the "self-referencing" techniques for determining and comparing thermal contrast for the pixels, as described in greater detail below. Then, knowing the contrast, the area and depth of a defect can be identified. Accordingly, a defect may be localized by both specific coating layer and area. In other words, both the planar location and the depth of the defect can be determined in this embodiment.

The processor may then determine at step 132 whether the defect is repairable by comparing defect parameters with stored data of historic defect phenomenon. If the defect is not repairable, in one embodiment, the shell may be sent for scrap at step 134. If it is determined that the surface and coating is repairable, a technician may repair the defect at stage 136 or take other appropriate measures as discussed above.

It should be understood that the method illustrated in FIG. 4 may also be used for detecting defects in a single coating or shell, and therefore, is not limited to application with more than one coating. For example, referring to FIG. 3, wherein a single coating has been applied to the automobile shell, IR sensor may be configured to measure the actual changes in temperature during the measurement period and transmit the measurement to the processor for comparison with a thermal emissivity value (an expected change in temperature) for the shell, coating and defects. Accordingly, the method illustrated in FIG. 4 can be used to detect defects in both single-layered and multi-layered coatings by measurement and comparison of the detected speed of the change in temperature.

Figure 5:
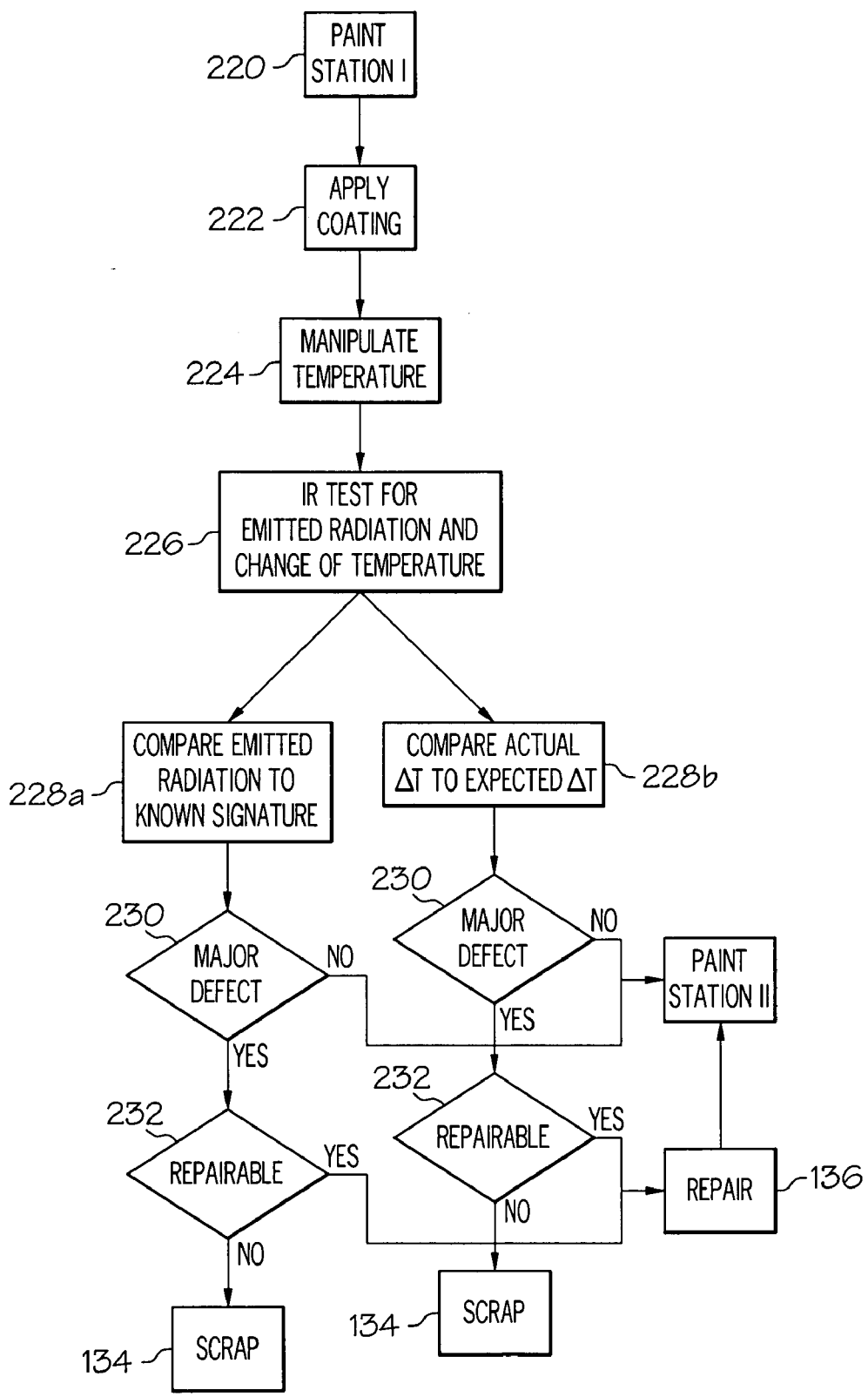
FIG. 5 is a simplified flow chart illustrating exemplary steps in another embodiment of the method of inspecting coatings in accordance with the present invention.

It is also contemplated by the present invention to combine the methods discussed above to further ensure absolute quality of the automobile coating method. For example, referring to FIG. 5, another embodiment of the method for inspecting multi-layered coatings is illustrated. Similar to FIGS. 3 and 4, a coating may be applied (at step 222) to the automobile shell at Paint Station I. Once the coating has been applied, the temperature of the automobile shell and coatings may be manipulated (step 224) as discussed above. Once removed from the curing oven, an IR sensor may take a field of view picture to measure the emitted radiation (the thermal profile) from the shell and the coating and may also measure the speed of the change of temperature of the shell and defects within the coatings 226. IR sensor may transmit the data to processor for comparison to stored data.

The processor may compare the thermal profile with the thermal signature of the automobile shell (at step 228a), an acceptable preexisting model profile, and/or, if later in the coating method, to the previous thermal profile to determine the presence of any defects. Likewise, the processor may compare the actual change in temperature to an expected change in temperature to determine the presence of any defects (step 228b). If desired, the comparisons can be evaluated at step 230 either together or separately to realize the true nature of the defect and whether repair is needed and/or practical.

Because the present systems and methods are capable of such detailed measurements and comparisons thereby yielding immediate detection of a defect, it is contemplated that the present invention may be integrated with other artificial intelligence and/or automatic feedback logic so that, once a defect is detected, statistical analysis of operation and necessary changes in coating methods (if any) can be made in real time. For example, referring to FIGS. 2 and 5, upon detection of a defect (i.e. paint over-spray), processor 40 may flag the defect on the current shell for repair, but also transmit a signal to application apparatus 50 at Paint Station I to decrease spray pressure, paint amount, clean or replace the spray gun, etc. (i.e. correct a detected defect). This information might also facilitate maintenance or upgrading of coating application systems by identifying problem areas. In addition, the processor may store and/or otherwise update the knowledge database regarding information about the defect, the operation of the machinery causing the defect and/or the technical operation of the machinery or station where the defect occurred. Accordingly, real time changes and statistical analysis can be made to minimize or eliminate defects, not only in coatings in previous stages, but in the entire coating method.

EXAMPLES

Introduction

The infrared inspection techniques discussed herein offer a flexible, non-contact and non-destructive tool for investigating the presence of defects in a variety of automobile manufacturing processes. As shown in the examples below, principles of the present invention can be applied for inspecting coated surfaces and/or the adhesion strength/integrity in welded composite polymer plastic joints.

In these examples, the type of infrared techniques that can be utilized can include use of transmitted signals and/or of pulsed reflected signals, for example. The detection and generation of the photothermal waves could be performed remotely providing a non-contact system and method. Due to the remote scanning and area inspection techniques used in these examples, the potential of improving the inspection time and of uses in realtime manufacturing operations can be attained.

Various heating methods can be utilized for such defect detection. It has been found that for the inspection of close to the surface, shallow adhesion interfaces, as in the case of the coating adhesion application, a step heating regime of infrared thermography that will monitor the heat rise across the material surface can be used. And for the cases of in depth defects or the inspection of subsurface defects in materials of low thermal conductivity as in a plastic bond application, it has been found that a pulsed reflected infrared thermographic setup can be utilized to provide a better quantitative analysis.

Equations:

As will now be described, the evaluation of adhesion integrity and coating defects using infrared thermography can be based on the concepts and principles discussed above. In particular, with respect to the film-substrate interface, these anomalies constitute planes that reflect the thermal wave by an amount governed by the thermal mismatch factor $\Gamma$ discussed above and which can also be defined as:

$$\Gamma = \frac{l_{coat} - l_{plane}}{l_{coat} + l_{plane}}$$

where: e is the thermal inertia or, effusivity; defined as:

$$e = \sqrt{k \cdot p \cdot c}$$

k is the thermal conductivity, p is the density and c is the specific heat of the material. The subscripts coat, plane refer to the coat material and the material that the reflection plane is made of (e.g. air) respectively.

The role of the thermal mismatch factor $\Gamma$ in reflecting thermal waves leading to heat entrapments over defects can be represented by the following heat conduction equation:

$$T(z=0, t) = C_c \cdot \sqrt{t}\left[1 + \sum_{n=1}^{\infty} -2 \cdot \Gamma^n \cdot \left\{\exp\left(\frac{-n^2 L^2}{\alpha_o t}\right) - \frac{nL\sqrt{\pi}}{\sqrt{\alpha_o t}} \operatorname{erfc}\left(\frac{nL}{\sqrt{\alpha_o t}}\right)\right\}\right]$$

where z is the depth, t is the time variable, $C_c$ is a constant related to the heat absorption, L is the thickness of material and $a_o$ is the thermal diffusivity defined as;

$$a = \frac{k}{p \cdot c}.$$

The solution can be expressed at depth z=0 which is the facial temperature history detected by the infrared detector. From the equation, it is apparent that Γ is the factor that decides on the heat travel forward and backward from the plane of reflection (defect or substrate interface) to the material surface affecting the facial temperature value.

Figure 6:
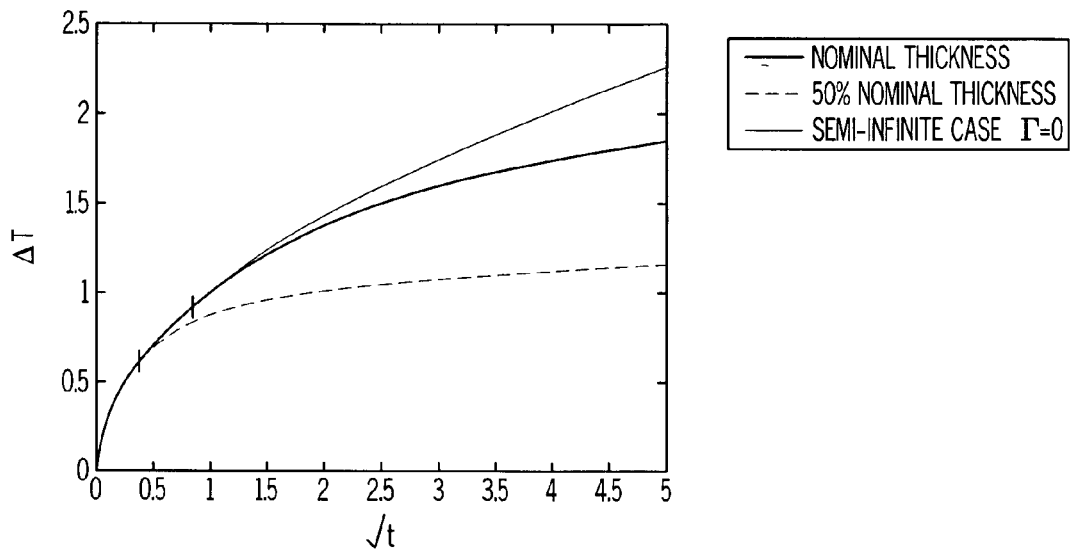
FIG. 6 and FIG. 7 are graphs showing how the change in temperature over time can be used to detect defects, according to principles of the present invention.

Illustrative Applications:

Thus, according to principles of the present invention, the thermal wave reflection effect from the substrate interface could be used for locating subsurface defects, as well as for measuring the thickness of a coat film. A thickness measurement application is illustrated in FIG. 6 where a temperature history graph (i.e., the temperature versus time) is shown for different illustrative paint layer thicknesses upon the reflection from a steel substrate. The thickness value could then be inferred from the time of on-set point of departure from the semi-infinite case (i.e. no, reflection interface).

Figure 7:
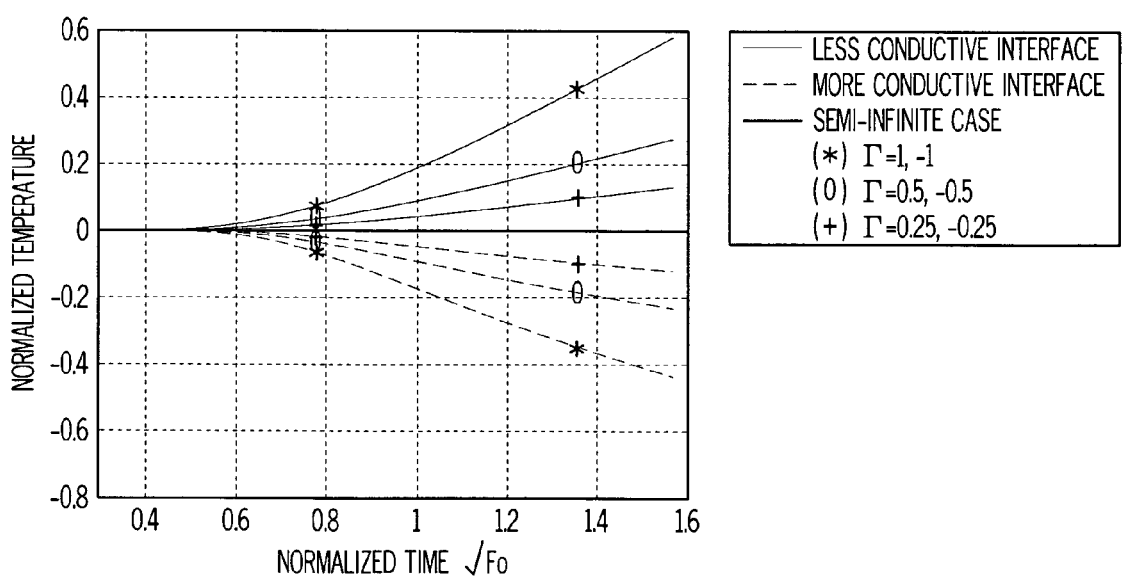
Figure 8:
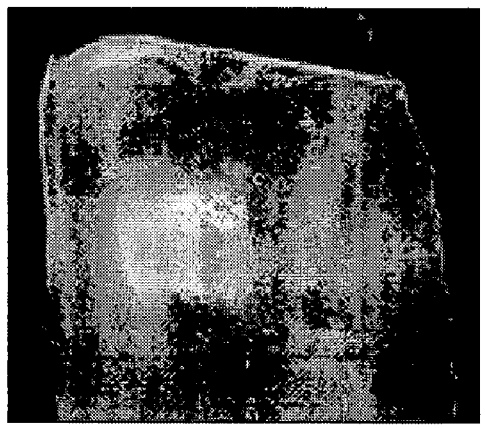
FIG. 8 shows an example thermal profile of a steel structure coated with an anti-corrosive protective coat with a chipped spot representing a different thermal profile from its surroundings, which can be detected according to principles of the present invention.
Figure 8:
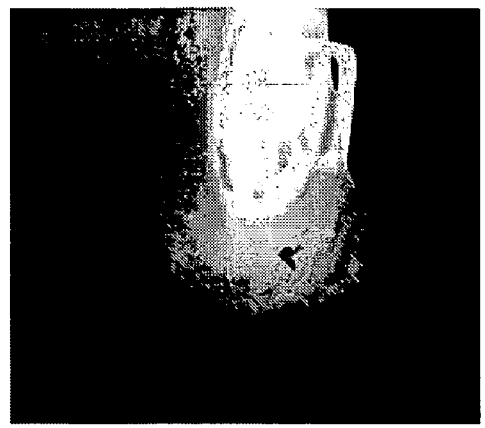

Similarly, the evaluation of the adhesion interface integrity can then be conducted utilizing a similar procedure of monitoring the value of Γ at a specific depth (at the adhesion interface) and characterizing the adhesion anomalies based on the thermal mismatch factor value. To illustrate this application, FIG. 7 shows the reflection from the adhesion layer interface with different Γ values. FIG. 8 is a plot of a normalized version of the above heat conduction equation, the normalization being done with respect to the heating source (i.e. $C_c$) and the normalized time represents the square root of the Fourier number $$Fo \left( \text{i.e. } t_{norm} = \frac{\sqrt{a \cdot t}}{L} \right)$$

Accordingly, monitoring thermal profiles over time, and in particular monitoring thermal mismatch in the profiles (i.e., monitoring changes in how one area of a profile differs from surrounding areas), can be used for both three dimensional subsurface defect identification, as well as for thickness measurement.

Accordingly, as shown above and described with respect to the more specific examples below, principles of the present invention can be used for inspecting and locating subsurface defects in coatings, surfaces, and adhesion interfaces. According to one aspect, monitoring thermal profiles over time, and in particular, monitoring changes in the thermal mismatch and/or thermal contrast exhibited by the thermal profiles, can be used for pinpointing the specific depth location of defects and/or defects in thickness.

More specific examples are provided below.

Example 1

Figure 9:
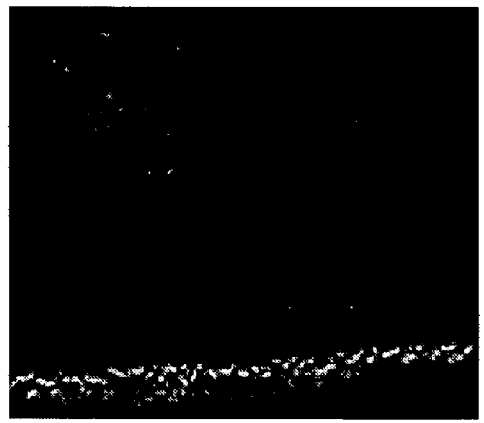
FIG. 9 which shows a visual image of a thin paint area and its corresponding thermal profile, which can be detected according to principles of the present invention.
Figure 9:
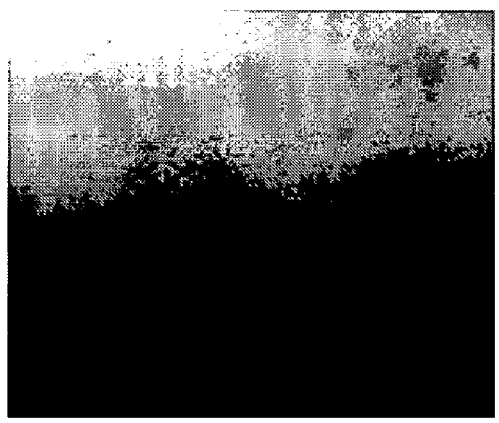

In this example, an infrared system is installed on a production line for the detection of a chipped spot in an anti-corrosive coating. FIG. 8 shows a thermal profile of a steel structure coated with an anti-corrosive protective coat with a chipped spot representing a different thermal signature from its surroundings. (The same infrared detection system can be used for missed coat spots (thin paint) detection.) Those chipped spots expose the steel substrate which has a different thermal inertia from that of the coat making it an easy target to detect. This application is shown in FIG. 9 which shows a visual image of a thin paint area and the corresponding thermal profile. In accordance with principles of the present invention, the change in temperature over time of the area can be determined by monitoring the thermal profile over time, and defects can thereby be determined based upon the change in temperature versus the expected change, such as according to the methods described herein.

Example 2

Figure 10:
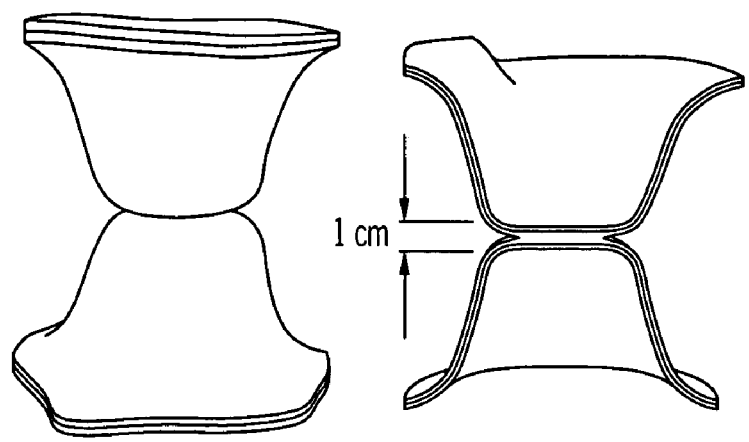
FIG. 10 shows an example of a bonded joint, the strength and integrity of which can be determined according to principles of the present invention.

In this example, an infrared system is used to investigate the adhesion layer integrity of a polymer plastic welded joint, according to additional principles of the present invention. The joints in this example are made from a composite of two layers of a polymer (High Density Polyethylene HDPE) with an adhesive interface. Carbon pigments have been added to one of HDPE layers for darkening to provide better thermal absorption and emission properties for insulation purposes. The geometry of the joints under inspection in this example, along with a cross section, are shown in FIG. 10, and the geometry of this example is represented as two cups welded together at the neck region. The bond interface is located between the HDPE layer and the rest of the geometry. In this example, the infrared thermography can be applied in two modes; a transmission mode where the stimulant (e.g., source) and the detector are located on opposite sides. For the reflection mode, the stimulant and detector are situated at the same side and monitor the reflected thermal wave effect on the surface temperature over time. The main aim of using the reflection mode is to investigate some of the subsurface features such as delaminations using a real time non contact mode.

Figure 11:
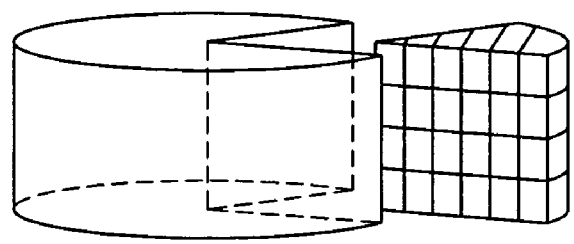
FIG. 11 is a three-dimensional analytical model intended to simulate the bond region of the example of FIG. 10.

An analytical model is devised in this example to help predict the behavior of this material. This analytical model is shown in FIG. 11 and is intended to simulate the bond region. This model utilizes an implicit finite difference approach to represent the general homogenous heat conduction equation in the following cylindrical coordinates equation:

$$\frac{\partial^2 T}{\partial r^2} + \frac{1}{r}\frac{\partial T}{\partial r} + \frac{1}{r^2}\frac{\partial^2 T}{\partial \Theta^2} + \frac{\partial^2 T}{\partial z^2} = \frac{1}{a}\frac{\partial T}{\partial t}$$

This symmetry simplifies the analysis to where only a pie slice is studied. The back and side walls are assumed to be thermally adiabatic. The stimulation boundary conditions are set according to a radiation source. The boundary conditions can be adjusted to fit the transmission mode. The convection and radiation surface heat losses are included in this model. The delaminations in the analytical study are modeled as an air layer that will constitute an interface to reflect the thermal characteristics waves due to the thermal mismatch existing between the polymer and the air.

Figure 12:
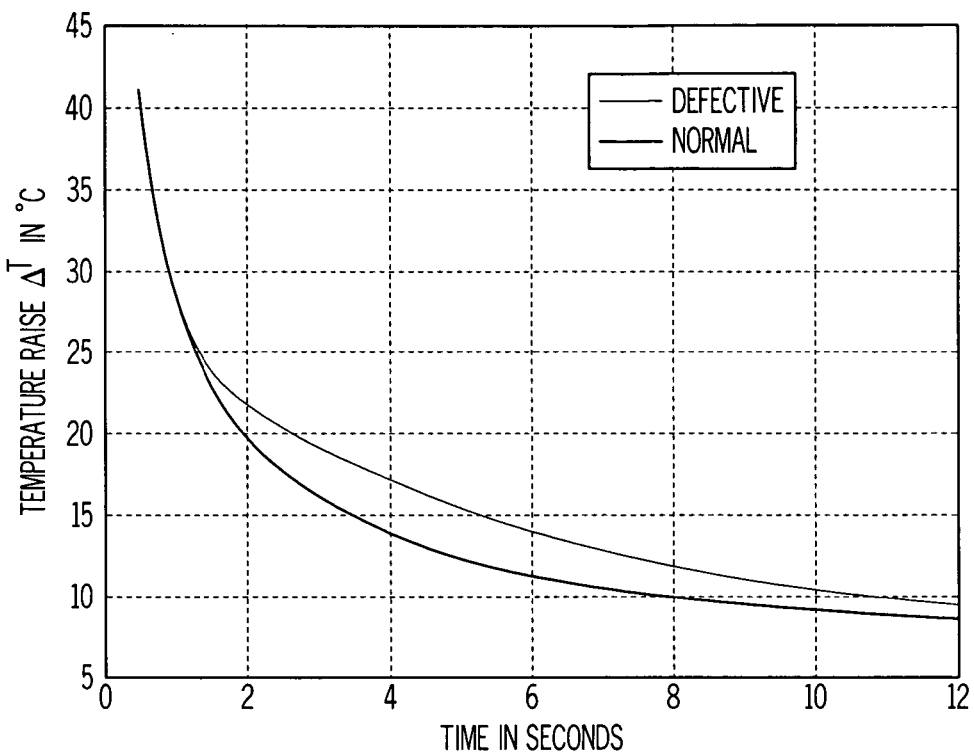
FIG. 12 is a graph showing a sample temperature cooling curve over time after depositing pulses at locations in a bonded joint, which can be used to detect the presence of an air gap according to principles of the present invention.
Figure 13:
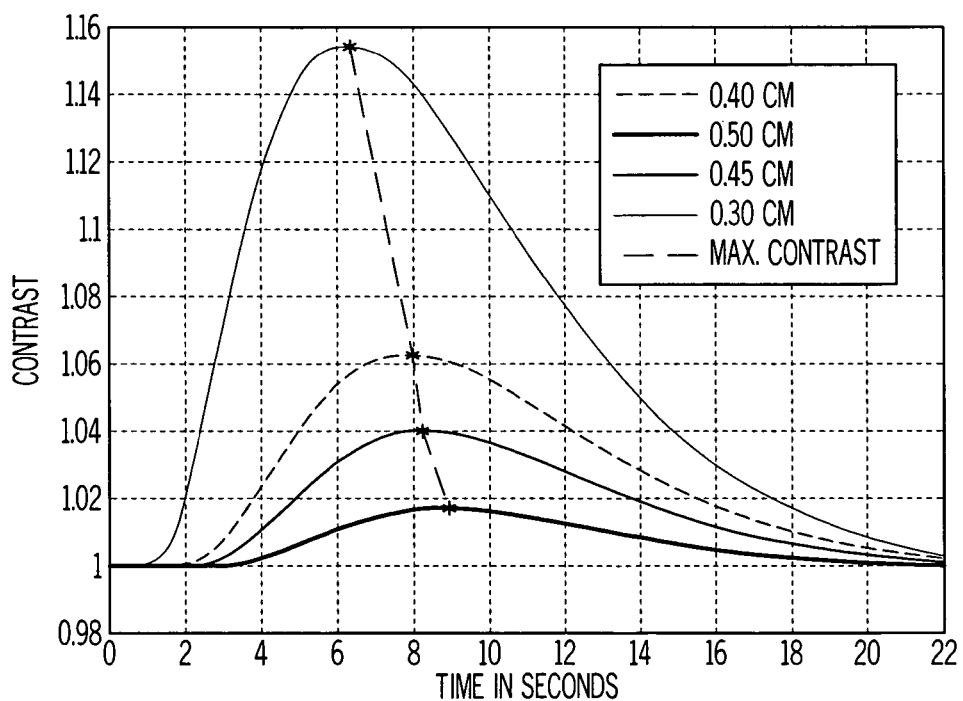
FIG. 13 is a graph showing the thermal contrast over time for different delaminations at different depths, which can be used to detect delaminations according to principles of the present invention.

The reflection of thermal waves from subsurface features affects the facial temperature value at that point causing a deviation from its surroundings. This deviation is monitored over time and recorded as the thermal contrast. FIG. 12 shows the sample cooling curve over time after depositing a pulse of Q=100 kW/m² over a non-defective spot and a second one over an air gap. FIG. 13 shows the thermal contrast over time for different delaminations occurring at different depths; as shown, the contrast peak decays as the depth of the delamination increases. FIGS. 12 and 13 can be used to guide the pulsed infrared thermographic procedure in deciding on the best observation time window for monitoring and recording the change in temperature over time, and the sensitivity limits.

Once recorded, the data can then be analyzed using different software routines; pulse phase thermography PPT, synthetic infrared thermography SIT, and/or infrared dynamic tomography IDT. The following analysis for this example is based on IDT with the intention of mapping the thickness of the adhesion layer of the kissing bond. This approach is based on establishing a maximum contrast matrix and a time-gram matrix. The maximum contrast matrix presents the maximum deviation values between a defective spot and a non-defective one exhibited through the transient response to the pulse and the time of occurrence for these values is reported by the time-gram matrix.

Moreover, in this example, a self-referencing procedure is utilized in computing the thermal absolute contrast needed for the maximum contrast matrix. The self-referencing procedure is based on computing the deviation between each pixel in the thermal profile and a small local neighborhood or area (e.g., a kernel of pixels) surrounding it. This procedure eliminates the need for a known sound area within the thermal profile for thermal deviation calculations and guarantees the accuracy since each thermal profile is referenced to itself. A computer code using MATLAB is prepared for the modified infrared dynamic tomographic calculations. A further modification is applied for the representation of the tomographic results to enable it for thickness mapping. The representation of this technique is based on slicing the material under inspection into depth slices that correspond to the distribution of the thermal properties at those depths. In this application the tomographic output will be represented in the form of a thickness map in order to include all the information in a single image rather than multiple slices. In this example, the thickness mapping scheme is applied using the following equation:

$$Z(i,j) = a \cdot \sqrt{t_{max}(i,j) \cdot C_{max}(i,j)^b}$$

where $Z(i, j)$ is the depth at location $(i, j)$, $a$, $b$ are constants determined experimentally (dependant on the material under inspection), $t_{max}(i, j)$ is the time at position $(i, j)$ taken from the time-gram matrix, $C_{max}(i, j)$ is the contrast value at $(i, j)$ from the contrast matrix. Accordingly, the depth can be determined from the contrast and the corresponding time that the thermal profile was taken to compute the contrast.

Figure 14:
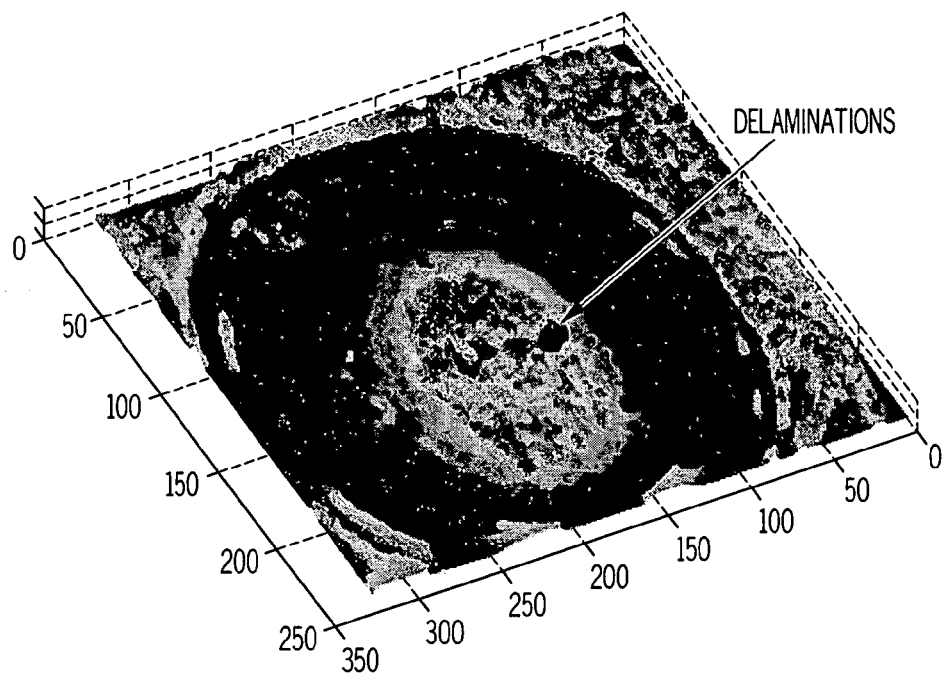
FIG. 14 is a thickness map showing a drop in thickness in the middle of a kissing bond joint, having delaminations which can be detected according to principles of the present invention.
Figure 15:
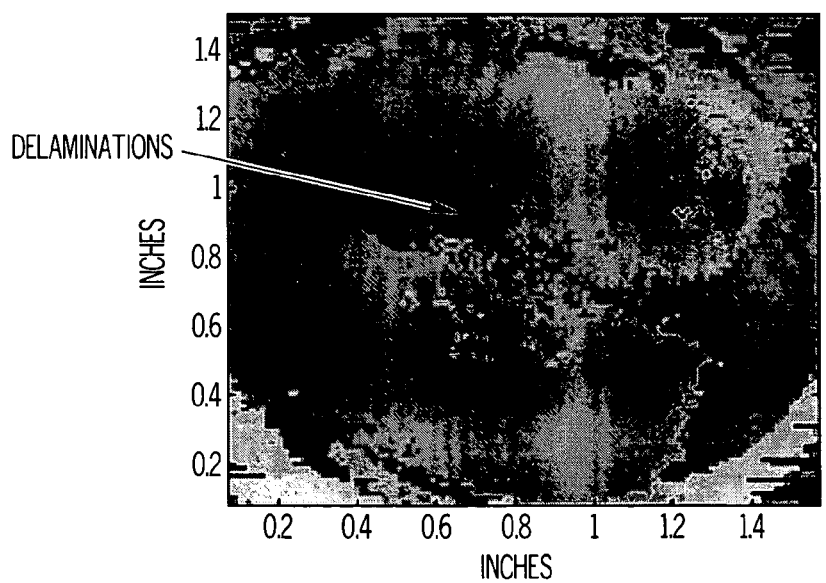
FIG. 15 is an image verifying the presence of delaminations in an example bonded joint.

The result of using this approach is shown in FIG. 14 which shows a drop in thickness map in the middle of the kissing bond, thus indicating delaminations. To validate this result, an ultrasound C-scan is conducted with an Ultrascan 5 (US Ultratek, Martinez, Calif.). For this scan the transducer frequency is 5 MHz, the sampling rate is 100 MHz, the X-Y scan increment is 0.012 inches, and the sonic velocity is 0.0741 inches/microsecond. The velocity of sound is estimated with a contact transducer applied over parts of samples including regrind and virgin layers that could be measured directly with calipers. The X-Y increment is chosen to be about ¼ the width of the beam field of the transducer (0.04 inches). The C-scan result is shown in FIG. 15 which verifies the existence of delaminations in this sample.

Example 3

In this example, and in accordance with additional aspects of the invention, infrared "self-referencing" thermography is again applied. As mentioned, this technique eliminates the need for prior knowledge of a defect free area to allow automatic identification of defects from thermal profiles. The basis of this technique is to divide the thermogram profile into small, localized neighborhoods using the assumption that these neighborhoods exhibit the non-defective behavior for the thermal contrast computation. This technique can be utilized in both static (hot spot detection) and dynamic (Infrared Tomography) cases.

The thermal contrast computation is used in processing the data in this example, because of its ability to enhance the image quality and consequently the defect visibility. Thus, contrast could be computed by monitoring changes in temperatures in multiple profiles taken successively. Many definitions could be used to compute the thermal contrast. Such definitions include the running contrast, normalized contrast and absolute contrast with the absolute contrast being the most widely used. Absolute contrast can be computed through the following equation:

$$C(i,j,t) = T_{def}(i,j,t) - T_{soa}(i,j,t)$$

Where $(i,j)$ are the coordinates of the pixel in the thermal profile, t is the time instant, $C(i,j,t)$ is the thermal absolute contrast, $T_{def}(i,j,t)$ is the temperature of the defective pixel, $T_{soa}(i,j,t)$ is a non-defective area temperature value.

However, the common problem with computation of the thermal contrast using any of these contrast definitions is the fact that they require prior knowledge of a non-defective area within the thermal profiles under study (i.e. $T_{soa}(i,j,t)$). Other problems with the thermal contrast computations arise from the non-uniform distribution of stimulant power on the surface of the material inspected and the uneven surface emissivity due to the surface geometry or condition (surface roughness and cleanliness). Computational problems are also present for continuous contrast measurements. Such problems complicate the automation of the infrared thermographic inspection and reduce the efficiency of automatic systems in evaluating some geometrical shapes.

The present technique of this example is based on comparing the behavior of a defective pixel with a kernel (21×21) of pixels surrounding it to study the deviation in the logarithmic temperature time history slope, in order to monitor the change in temperature over time of one area with respect to adjacent areas. The basic principle of this technique, which will be referred to as "self referencing", is to divide the thermal profile data for the pixels representing the surface into small local neighborhoods to serve as the non-defective behavior required for the thermal contrast computation. The contrast is then computed through the following equation:

$$C(i,j,t) = T_{pix}(i,j,t) - T_{surr(i,j)}(t)$$

Where: $T_{pix}(i,j,t)$ is the temperature of the pixel at i,j coordinates and time t, $T_{surr(i,j)}(t)$ is the average temperature of the neighborhood surrounding the pixel (i,j) at time t. Thus, this method subtracts the pixel temperature from that of the mean for the surrounding pixels. Then, each difference for each pixel can be compared to particular multiples of the standard deviation of the surrounding neighborhood to decide if the pixel is defective. If this difference is larger than the criterion (determined for the particular application), then the pixel is defective. If it is smaller, then it is not defective. Accordingly, this calculation can be made statically on a particular thermal profile, rather than continuously over time.

Other applications of this approach could use the median of the surrounding neighborhood temperatures rather than the average. Application of this approach overcomes challenges resulting from non-uniform heating and uneven emissivity on the surface of materials under inspection. Breaking the thermal profile into small enough local neighborhoods to ensure uniformity in power distribution and emissivity values eliminates the influence of unevenness. The following four main advantages can be gained through applying the self-referencing procedure of this example:

(1) Eliminates the need for separate "standard reference" since each thermal profile will be referenced to itself.

(2) Overcomes non-uniformity in the delivery of stimulant power, uneven emissivity and geometrical differences.

(3) Eliminates the need for prior knowledge of a defect free area within the thermal profiles.

(4) Simplicity and static operation, which leads to relatively short processing time.

To maximize the accuracy of defect detection, the size of the local neighborhood can be selected such that it will be larger than the defect and sizes sought and assure a stable temperature across the region, but small enough to be contained within the smallest area of non-uniformity.

To illustrate the effectiveness of the self referencing scheme it will be applied to a static infrared thermographic hot spot detection and dynamic infrared tomographic application with different types and sizes of defects involved in the following more specific examples.

Example 3A

In this example, an infrared system is designed to detect facial features on metallic surfaces painted with automotive coating structure (120 μm in thickness). Such features may include dust particles, dents and foreign matter contamination which will affect the appearance of painted surfaces. Those imperfection areas will have a different thermal profile (as well as a different change in temperature over time) when compared with their surroundings, due to the difference in the thermal properties (dust or dirt contamination) or, difference in the emissivity due to the geometry (dents).

This example is intended to inspect large fields of view in real time, creating a challenge to assure delivery of uniform heat to the entire field of view. In this example, a steel substrate sample is painted with 3 different types of paint (primer coat, clear coat and a third coat that contains metallic flakes). This coat combination is chosen to provide three regions with different thermal profiles. The primer coat is thick and opaque, the clear coat is a transparent layer and the third layer has metallic flakes that boost its thermal conductivity. A small indentation (dent) is artificially applied on the surface, size of dent=0.75 mm to provide a detectable defect.

Figure 16:
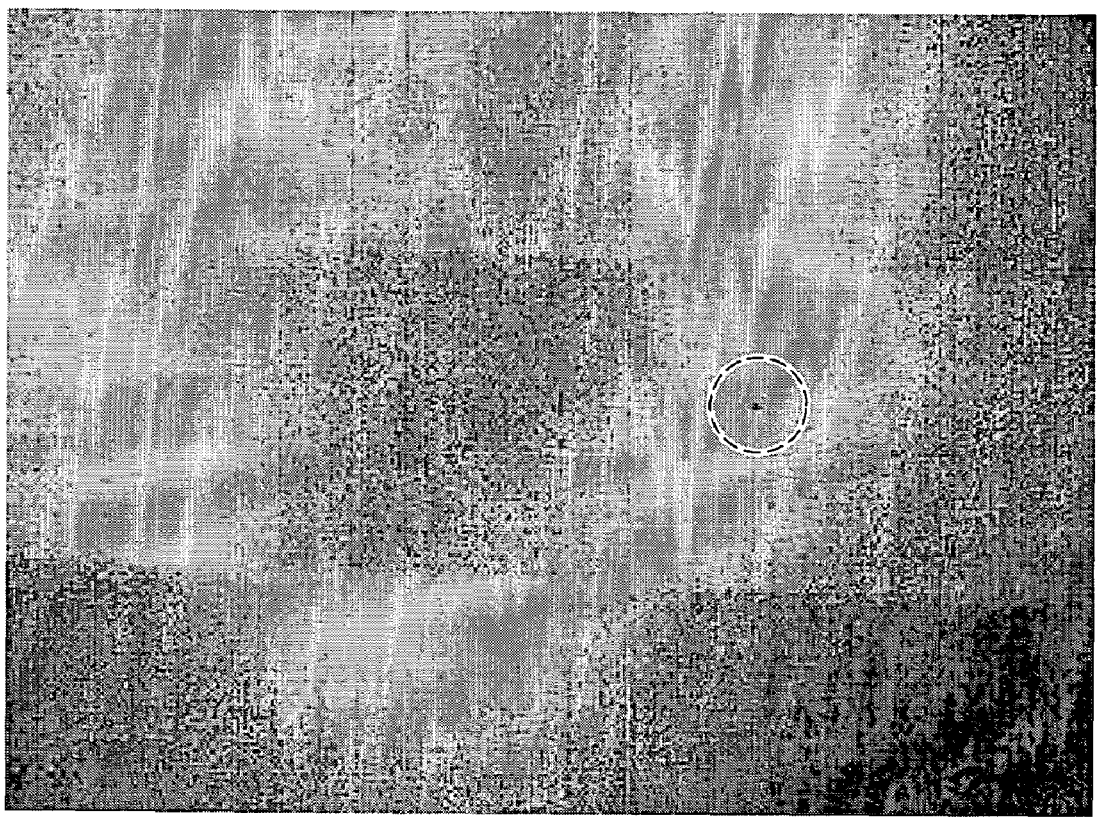
FIG. 16 is a thermal profile of an example coated surface, defects on which can be detected according to principles of the present invention.
Figure 17A:
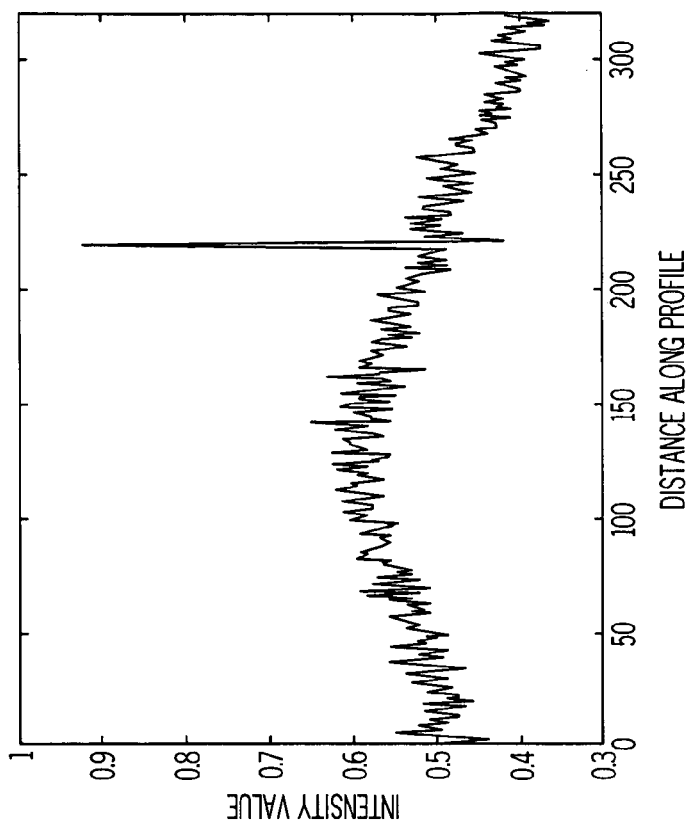
FIG. 17 are images and graphs showing examples of the contrasts and intensities present across a dent in a surface, FIG. 17a showing the contrast and intensity computed using an embodiment of a self-referencing technique, and FIG. 17b showing an absolute contrast and intensity embodiment.
Figure 17A:
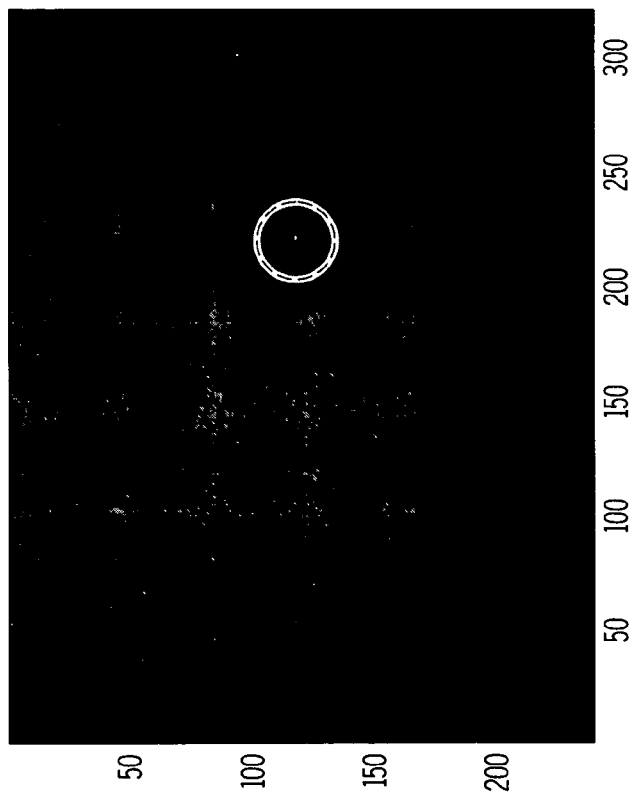
Figure 17B:
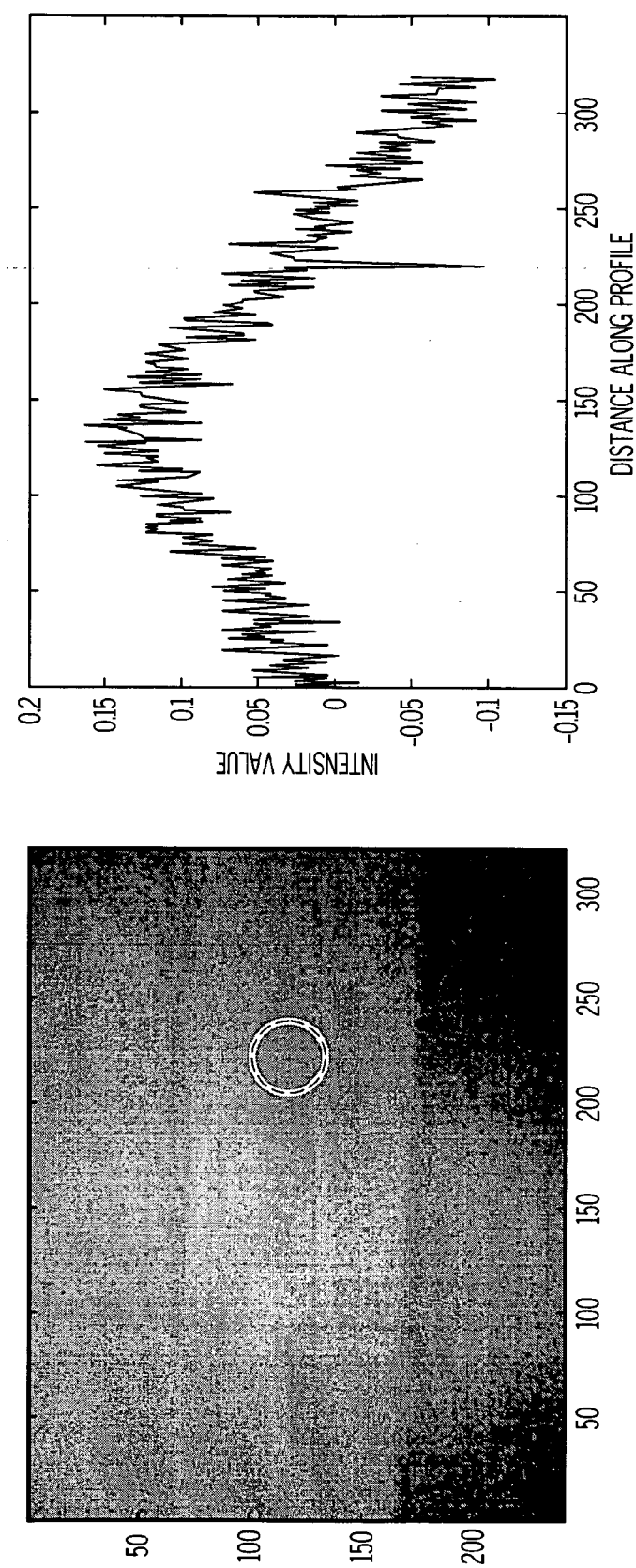

The sample is heated randomly (for 15 seconds) using a halogen lamp (150 watt) and the thermal map (picture) of the surface is recorded using an infrared bolometer, and in particular using a ThermaCAM SC 2000 product of FLIR, with 200 μm Germanium lens. The raw thermal profile image is depicted in FIG. 16. The thermal contrast is also computed using two approaches; one using the absolute contrast with prior knowledge of a defect free area within the thermal profile data (requiring operator intervention) and the other using the self-referencing approach. The results of the two procedures are shown in FIGS. 17a and b, with 17a showing the contrast across the dent using self-referencing technique, and 17b showing an absolute contrast. A profile of intensity values is drawn next to each of FIGS. 17a and 17b to show the contrast obtained with both techniques.

The self referencing algorithm of this example is oriented to boost the intensity of pixels that exhibit deviation levels from their local neighborhoods, which exceed criterion like the one shown in the following equation while preserving the rest of the pixels values. The technique can be utilized along with various embodiments of the present invention, including those which determine the change in temperature over time of the coated surface. In this example, the local neighborhood size is chosen to be a kernel of 19×19 pixels.

$$\eta \cdot \sigma_{surr(i,j)}$$

Where $\eta$ is a constant dependant on the signal to noise ratio of the thermal profile, and $\sigma_{surr(i,j)}$ is the standard deviation of the local neighborhood surrounding pixel (i,j).

Figure 18:
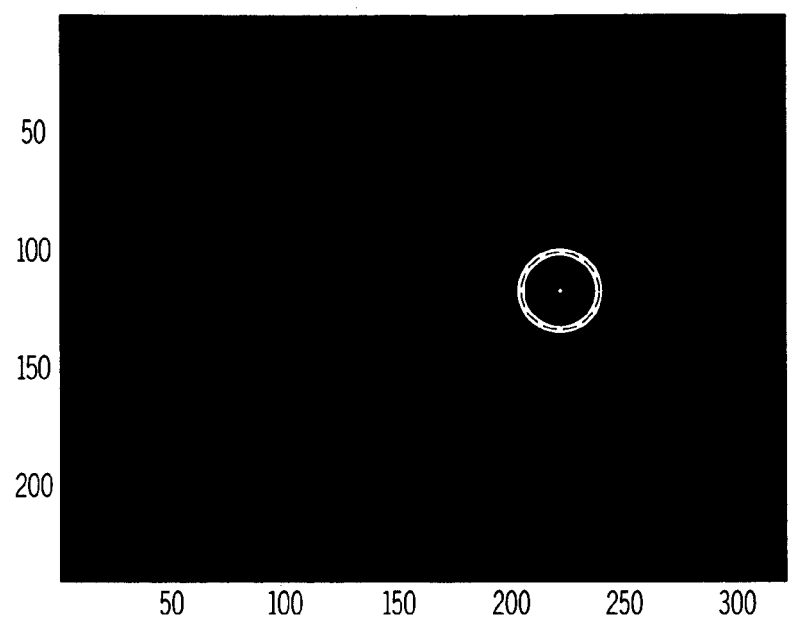
FIG. 18 is a graph showing the effectiveness of a self referencing approach in isolating the features of interest from the rest.

Such criterion could be used to threshold the thermal profile reducing the data content to the useful ones only, and can be used as an automated detection scheme. Applying a thresholding step according to the equation criterion to the thermal profile from FIG. 16 results in FIG. 18 which shows the effectiveness of such approach in isolating the features of interest from the rest. The thresholding process removes the middle strip and its edges completely since the local neighborhood size is set smaller than the strip width and so, such neighborhoods are contained within the strip.

Example 3B

Figure 20:
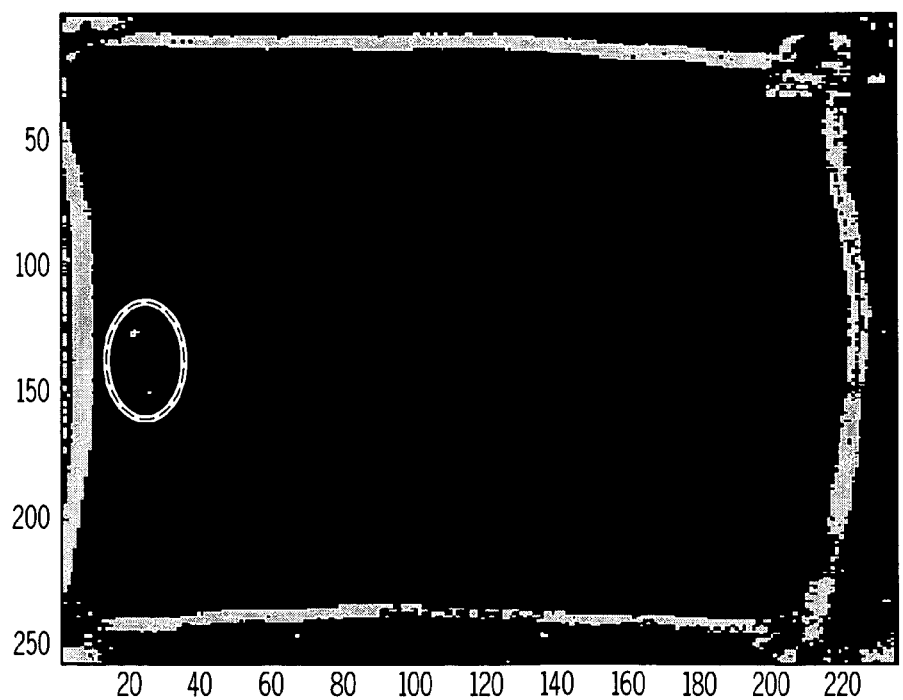
FIG. 20 is a defect graph, both showing defects in another sample which are detected using a self referencing technique according to principles of the present invention.
Figure 19:
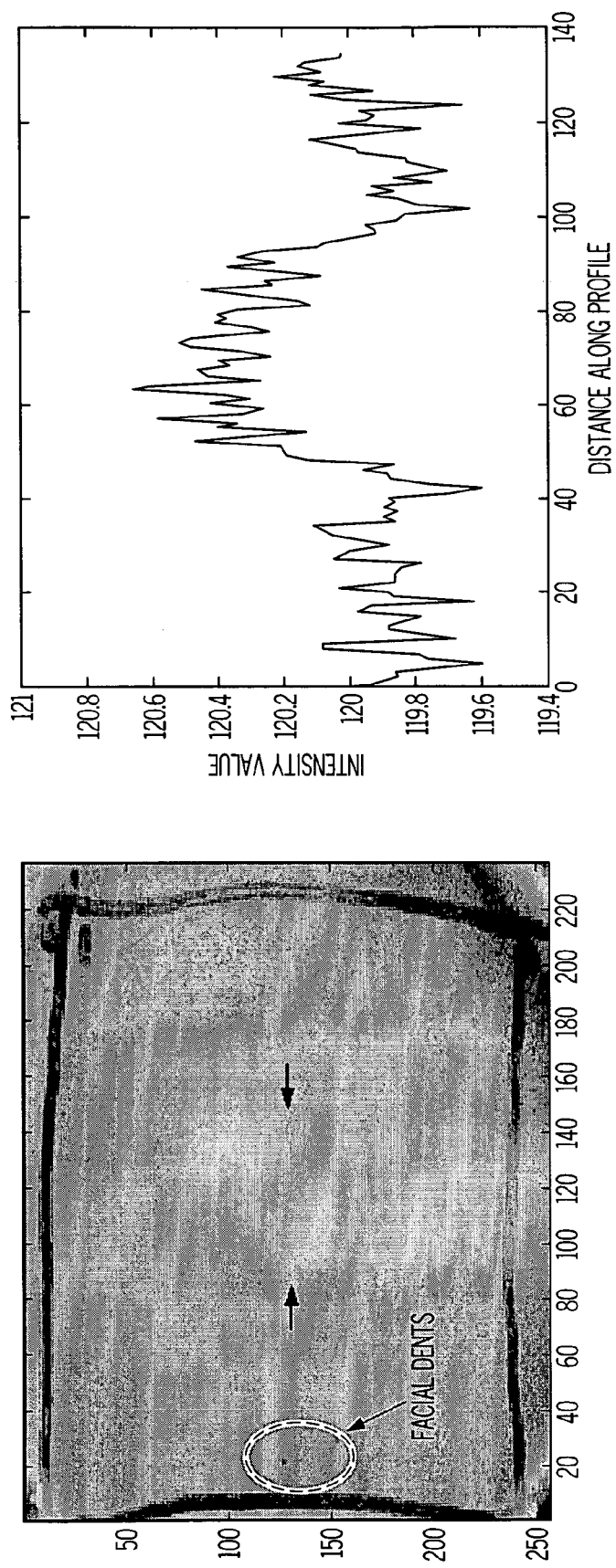
FIG. 19 is a thermal profile and its corresponding intensity graph.

To emphasize this feature of the self-referencing technique another sample with facial defects and large thermal mass is studied. This sample is shown in FIG. 19 and the results are shown in FIG. 20. Having large thermal masses disrupts the thersholding statistics based on the thermal profile as a whole which will reduce the effectiveness of an automated defect detection algorithm dependant on such statistics.

Example 3C

In this example, the self-referencing technique is applied to infrared tomography. The tomographic approach is chosen because it is based inherently on the monitoring of the thermal contrast transient behavior. The self-referencing algorithm is applied inside the tomographic procedure to assist the analysis of that behavior. The application case in this example is the inspection of the adhesion integrity in a welded plastic composite structure (High density polyethylene polymer). A pulsed infrared thermographic setup is utilized in this example using a 6.4 kJ pulse source with duration of 15 ms (commercial name BALCAR Source 6400). The sample shown in FIG. 10 is utilized in this example.

A computer algorithm using MATLAB is prepared to perform the infrared tomographic procedures for the sequence of thermal profiles obtained from the pulsed routine adopting the self-referencing contrast computation scheme. The local neighborhood (area or kernel) size in this case is chosen to be 33×33 pixels. The output from the tomographic routines is in the form of a time-gram image representing the time for the maximum contrast and the value of maximum contrast corresponding to that time. In other tomographic applications the time for the half maximum contrast can be used. In traditional presentations of infrared tomographic results the material under inspection is sliced into depth layers corresponding to the distribution of thermal properties at specific depths. In this example, a new form to represent the tomographic results is used. The thermographic data is represented as a thickness map for the area under inspection. This map represents all of the data in single image rather than the different slices for different depth layers. This image is created through adopting the time-gram and maximum contrast matrices into the following equation:

$$Z = \sqrt{\alpha_0 \cdot t_{min}} \cdot \left[\frac{e}{e_o}\right]^{0.95}$$

Where Z is the depth of the defect, $t_{min}$ is the occurrence time of the minimum of the normalized effusivity $$\frac{e}{e_o}$$

curve, which could be related to the time of maximum contrast. This equation could be written in terms of contrast terms as the following equation, as discussed earlier:

$$Z(i,j) = \alpha \cdot \sqrt{t_{max}(i,j)} \cdot C_{max}(i,j)^b$$

Where $Z(i,j)$ is the depth at location $(i,j)$, a,b are constants determined experimentally (dependant on the material under inspection), $t_{max}(i,j)$ is the time at position $(i,j)$ taken from the time-gram matrix, $C_{max}(i,j)$ is the contrast value at $(i,j)$ from the contrast matrix.

The results of the tomographic procedure have been shown in FIG. 14, which shows a delamination in the middle of the welded bond. To verify the existence of these delaminations an ultrasound check for the thickness map is used. The ultrasound device used a transducer frequency of 5 MHz, and sampling rate of 100 MHZ (commercial name Ultratek). The ultrasound result has been shown in FIG. 15.

Accordingly, the self-referencing algorithm works effectively in the dynamic thermal absolute contrast computation. This self referencing technique can help automating both static and dynamic infrared thermography applications without the need for operator intervention. Further, this technique may be used for inspecting complicated geometries.

As can be understood, the functionality of this algorithm and the other functionalities, methods, and algorithms described herein can be implemented using software, firmware, and/or associated hardware circuitry for carrying out the desired tasks. For instance, the various functionalities described can be programmed as a series of instructions, code, or commands using general purpose or special purpose programming languages, and can be executed on one or more general purpose or special purpose computers, processors or other control circuitry.

Example 4

In this example, a system is provided for detecting missed coated spots on steel substrates (fuel tanks, steel structures, etc.) utilizing the difference in their thermal emission. The system comprises a thermal detector, a scanning mechanism to transverse the detector across the target surface, a thermal manipulation device applied through a radiation source such as a heating lamp or through convection devices such as air guns or curing ovens which are existent in the process, and a computational processing unit. As discussed, it is believed that the difference in thermal emission over time is caused by the difference in thermal properties i.e. thermal conductivity κ, specific heat $C_p$ and density ρ between the missed spot that has the properties of those of the steel substrate and the well coated surroundings having the properties of the paint material. Upon the thermal manipulation (through any of the above thermal stimulation methods) of the coated steel product, the missed coated spots will store and transfer heat differently from their well coated surroundings leading to a different thermal imprint of those spots and differences in thermal changes which take place over time between the missed spot and the well coated surroundings. The thermal detector will detect the thermal emission from the coated surface and produce a thermal profile of this emission. The processing unit processes this thermal profile and detects the deviation of the thermal emission values that deviates from those of a well coated substrate, as well as the differences in thermal changes which take place over time. This information can then be utilized to detect the missed spot, such as according to the systems and methods described herein.

Figure 21:
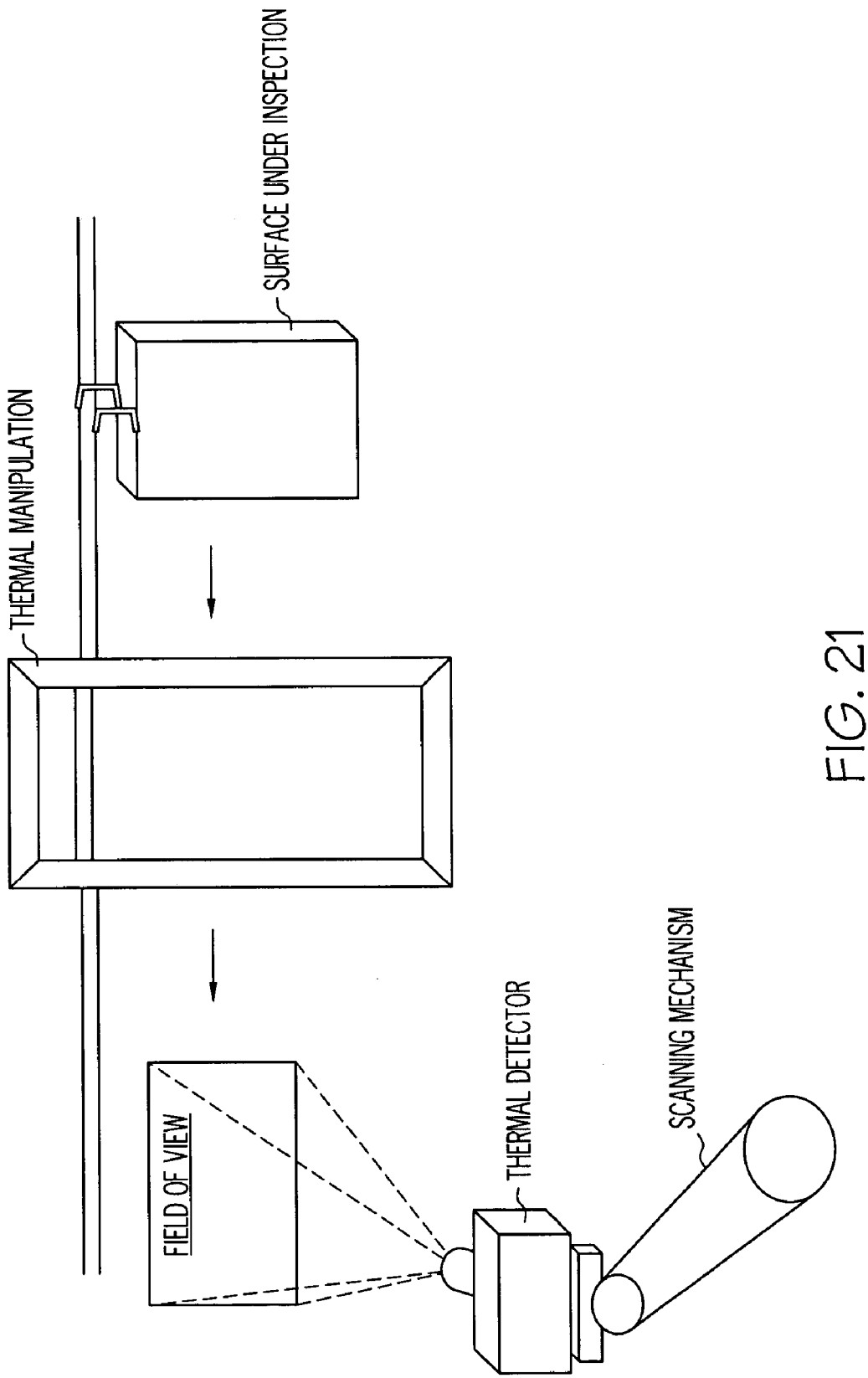
FIG. 21 is a schematic diagram of another illustrative system layout, the system being configured and operating according to principles of the present invention.

An exemplary system layout is shown in FIG. 21. In this example, steel fuel tanks are coated with anti-chip coating for protection purposes, but the painting application step (painting gun nozzle configuration) misses some spots termed as "thin paint spots". The thermal detector installed at the exit of the curing oven produces a thermal emission image of the tank and a computer code detects the thin paint spots based on their emission, and in particular using the differences in thermal changes which take place over time versus the temperature change that is expected over time.

Example 5

In this example, the integrity of plastic joints is inspected. The system utilized inspects the contact strength of the plastic molded joints, and the existence of delaminations at the adhesion interface. The system comprises in this example a thermal detector, a scanning mechanism to transverse the detector across the target surface, a thermal manipulation method, and a computer or processing unit. Well contacted joints (i.e. no trapped air) transmit heat faster than joints with air pockets because of the high thermal resistance of air (due to its low thermal conductivity value). So, monitoring how the heat travels through the joints over time aids the evaluation of the contact strength. In addition, delaminations have different thermal properties (i.e. thermal conductivity κ, specific heat $C_p$ and density ρ) and constitute interfaces that reflect the thermal front by an amount governed by a factor termed as thermal reflection coefficient $$\Gamma = \frac{\sqrt{k\rho c_{p_{Features}}} - \sqrt{\kappa\rho c_{p_{surroundings}}}}{\sqrt{k\rho c_{p_{Features}}} + \sqrt{\kappa\rho c_{p_{surroundings}}}}.$$

Figure 22:
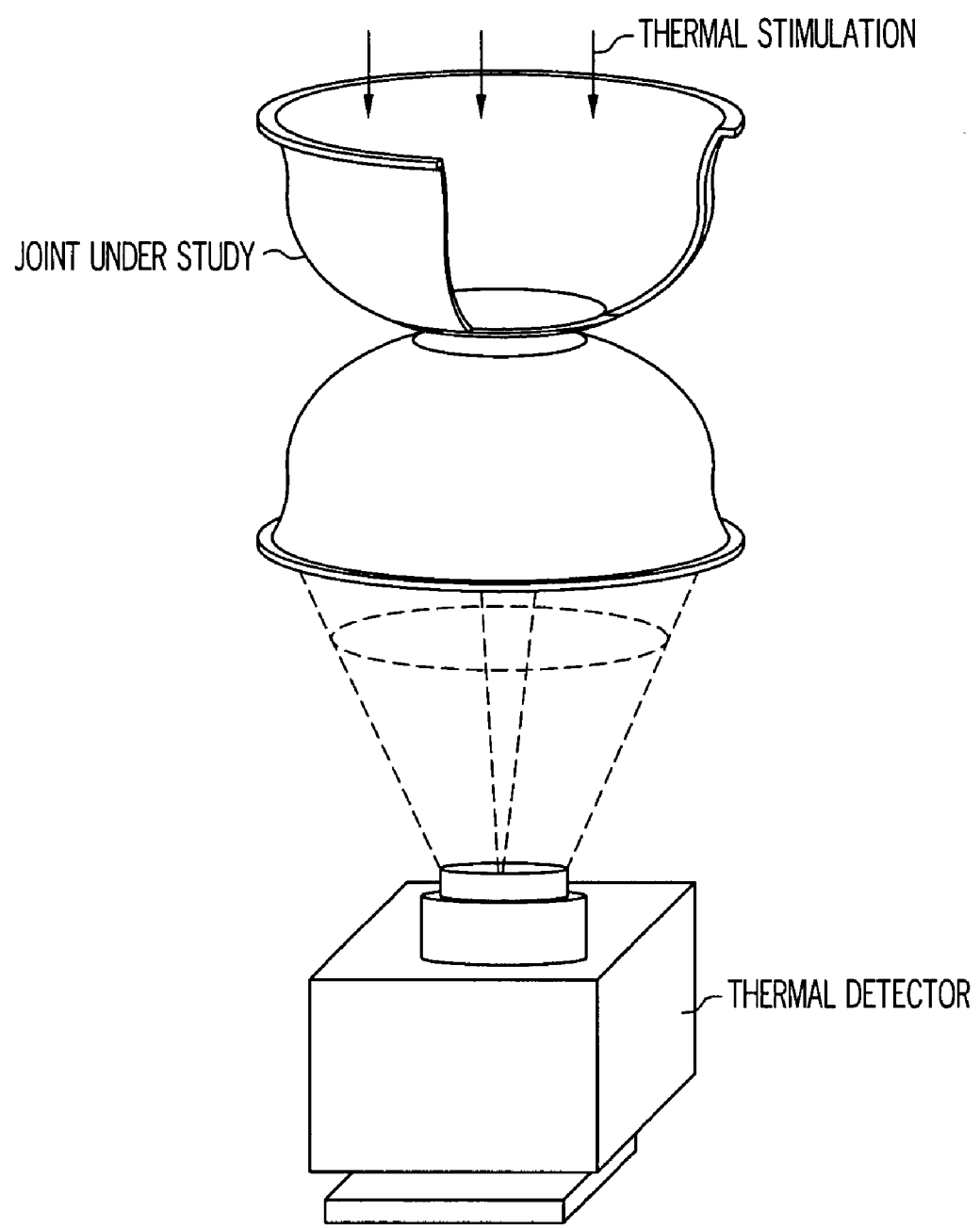
FIG. 22 is a schematic view of a system for detecting defects in a bonded joint, the system being configured and operating according to principles of the present invention.

This system could be applied in two configurations, one having the thermal detector and thermal stimulant at opposite sides and monitoring the thermal transmission through the joint under study, such as is shown in FIG. 22. The speed of the thermal front across joints changes with different strength values of the joint (measured by pull force required to break joints), and this concept is shown in FIG. 23.

Figure 23:
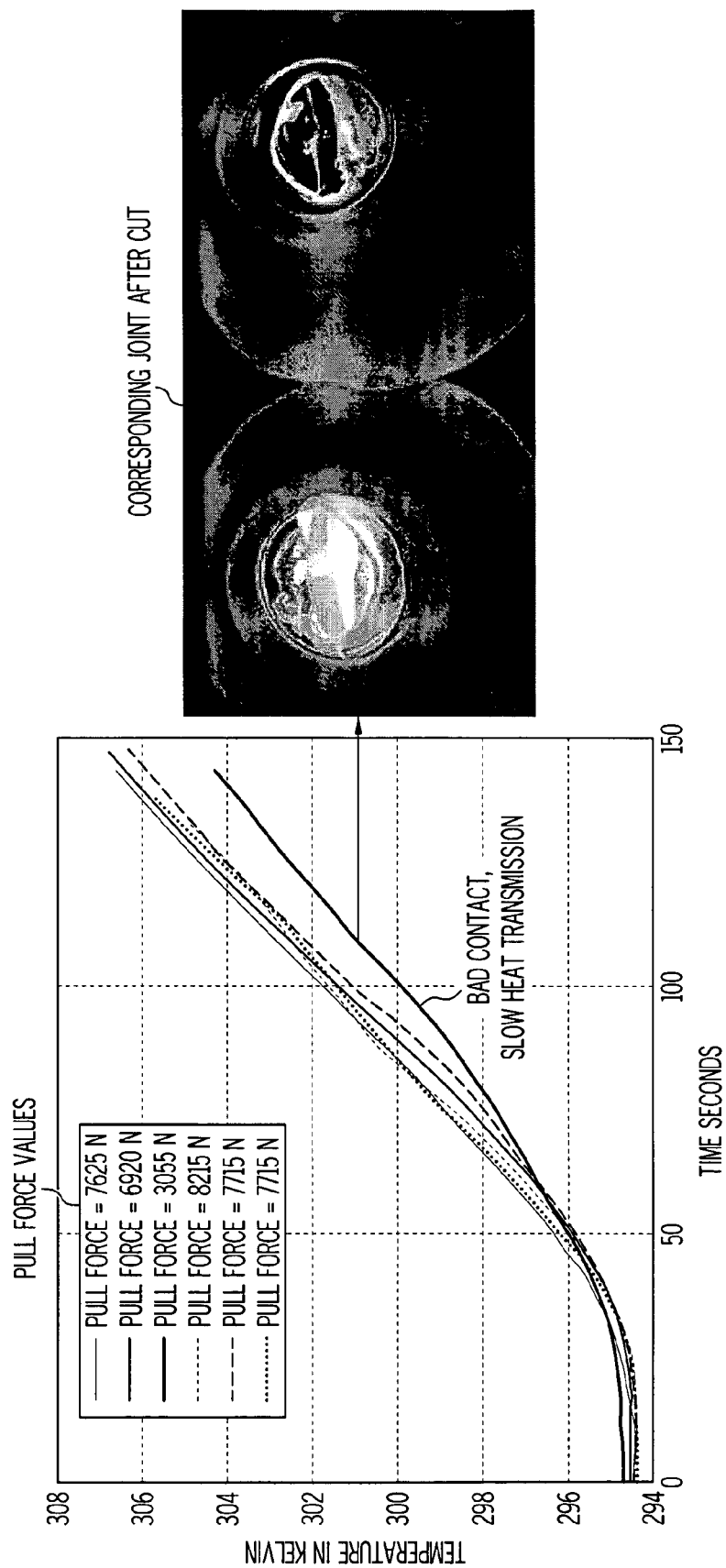
FIG. 23 is a graph illustrating the speeds of thermal fronts as the temperature changes over time for a plurality of samples, which can be used for detection of defects according to principles of the present invention.

Accordingly, as shown by FIG. 23 by monitoring the change in temperature over time as the joint is heated, it can be determined if an imperfection in the joint exists. In particular, a weak joint raises its temperature more slowly than a strong joint due to the presence of the air pockets.

Figure 24:
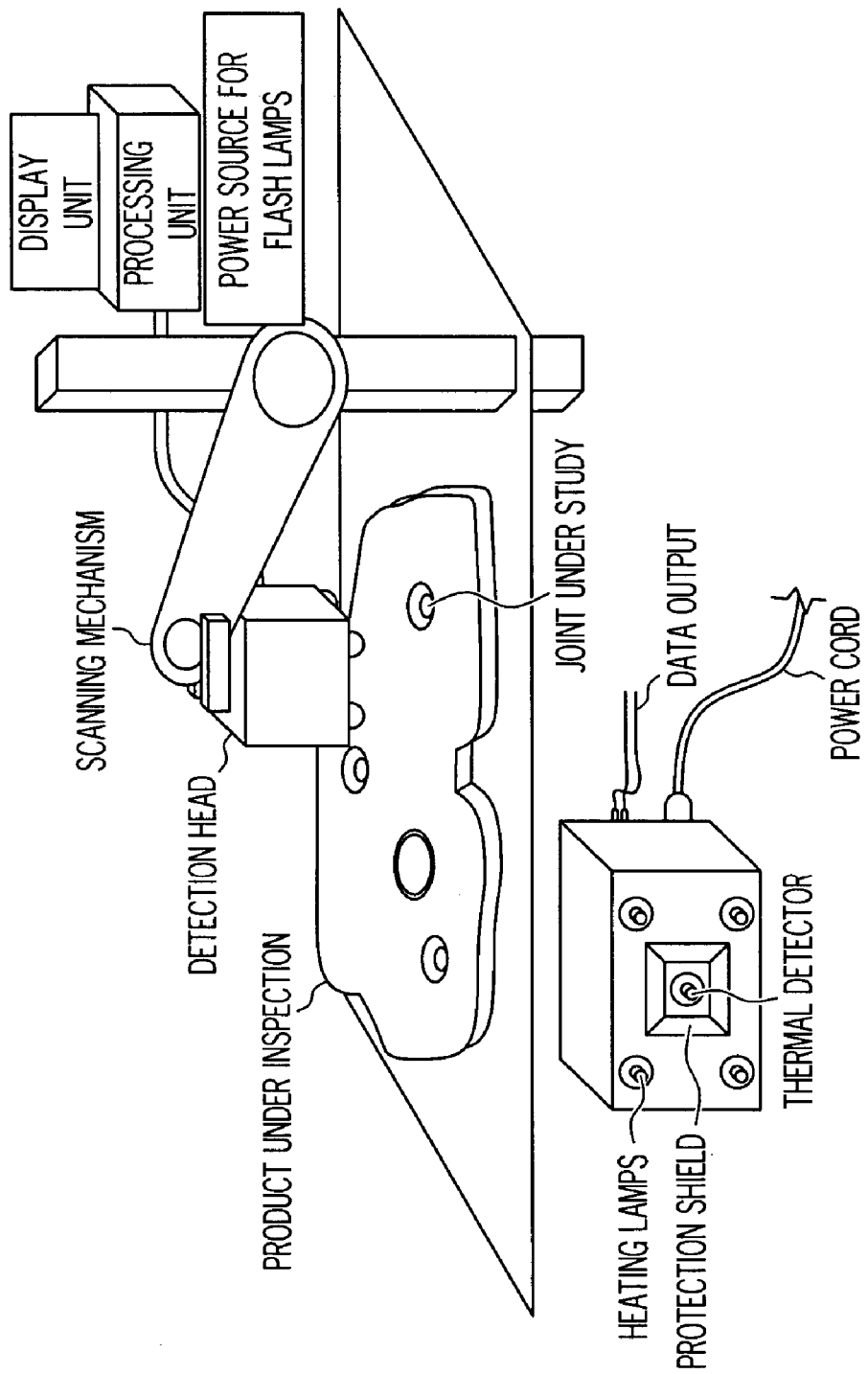
FIG. 24 is a schematic view of another exemplary detection system, configured and operating according to principles of the present invention.

The second configuration of this system could be applied through having the detector and thermal stimulant at the same side. So, in this case, the thermal detector monitors the reflected component of the thermal front rather than the transmitted. This configuration setup is shown in FIG. 24. The reflected thermal front reveals the interfaces or, features of reflection inside the joints and the time required for this reflection is an indication of these interfaces depth. The processing unit relates the amount of reflection and its time of occurrence to the material thermal diffusivity $$\alpha = \frac{\kappa}{\rho c_p}$$

to produce depth maps of those features as shown in FIG. 6. using the following equation:

$$depth = C\sqrt{t_{relfection}} \cdot S^n$$

C, n constants dependant on material thermal properties i.e. α. S thermal reflection signal. Accordingly, a relationship exists between depth and the thermal reflection signal obtained at various times.

As another example, plastic fuel tanks incorporate stand offs to protect tank structural integrity against crushing (vacuuming) or crashing (impact damage). These stand offs are made through plastic joints that should withstand a certain pull force before breaking. The methods and systems described above could be utilized for inspecting the structural integrity of such stand offs.

Example 6

In this example, a system is provided for evaluating curing performance in terms of curing uniformity and sufficiency. The system comprises a thermal detector, a scanning mechanism to transverse the detector across the target surface, a thermal manipulation device, and processing unit. The curing process is applied to dry the moisture content in the coat structure and catalyze the paint bonding. Monitoring the thermal emission with a thermal detector from the cured coated products provides temperature values for the product surface. This profile indicates the distribution of thermal stimulation provided by the curing oven. The temperature values in the thermal profile indicate the moisture content in coat structure since water has different thermal properties (i.e. thermal conductivity κ, specific heat $C_p$ and density ρ) from that of paint. This system could include a thermal detector installed at the exit of a curing oven to collect the thermal emission from the cured coated products. This thermal emission is processed to be compared with predefined (expected) ideal curing profile. This ideal profile is obtained through the thermal profile from a controlled sample.

Example 7

Figure 25A:
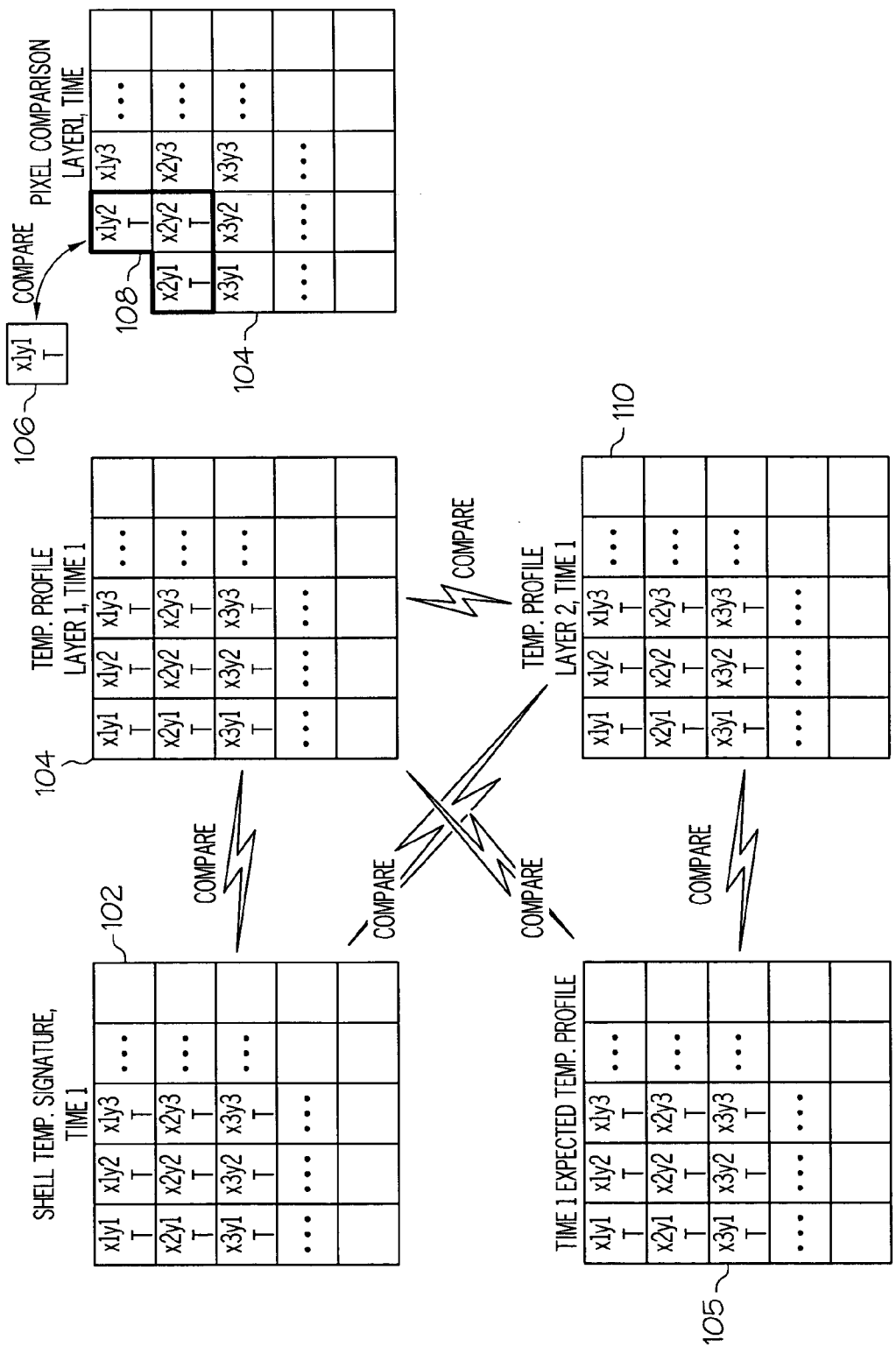
FIG. 25 is a schematic view of a combination of comparisons that can be made to locate surface and subsurface defects, according to various principles of the present invention.
Figure 25B:
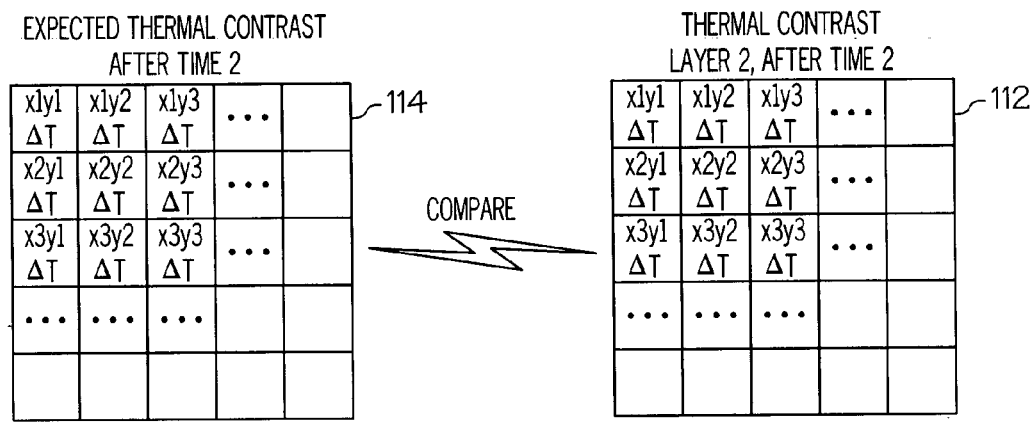
Figure 25B:
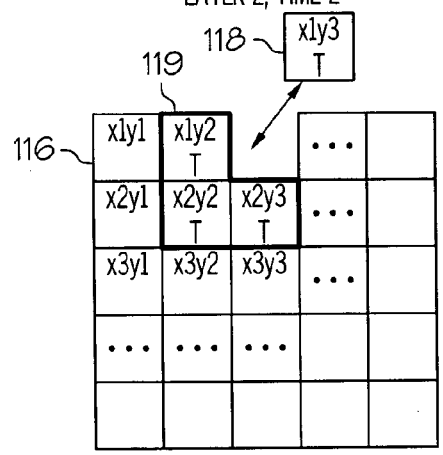

FIG. 25 is a schematic view of a combination of comparisons that can be made to locate surface and subsurface defects, according to various principles of the present invention. This example combines various aspects of the present invention to create a system and method for determining defects in surface coatings using multiple defect checking operations. In this example, the surface of an automobile part is coated with layers, and, for each layer, comparisons are made in order to determine the presence of defects. In particular, prior to applying the first layer, a shell thermal profile, or signature, 102 is obtained of the uncoated shell (e.g., coated with only primer) by heating the shell at a desired temperature for a given amount of time, and then using an infrared sensor to obtain the thermal profile. The shell thermal profile data 102 comprises a plurality of pixel locations representing the temperature T at each location XnYn on the shell.

Then, a first coating is applied to the shell, and the coating is heated at the same temperature and for the same amount of time as the shell. The thermal profile data 104 for the shell with the first layer is then taken at time t1, by using an IR sensor. This coating thermal profile data 104 is then compared to the shell profile data 102 to determine how significantly each pixel deviates from its corresponding pixel in the original profile taken from the shell. Should the temperature for a pixel in shell profile 102 exceed a corresponding pixel in the coating profile data 104 by a predetermined amount (dependent upon the application), then a potential defect at that pixel location is noted. As an additional check, each pixel in the coating profile data 104 may be compared to surrounding pixels in the data to determine whether any significant deviations are present. In particular, in this example, the temperatures T for the surrounding pixels 108 are averaged and pixel 106 is compared with that average. The number of surrounding pixels 108 to be used in the calculation can be varied depending on the application and the type of defects typically encountered. For example, defects in coatings on a fuel tank may be typically less than 5 millimeters in size, and so an appropriate number of pixels can be chosen that corresponds to 5 millimeters. Once a pixel 106 is compared to the average of its surrounding pixels 108, a thermal contrast can be calculated for each pixel representing the difference between those values. The thermal contrast for each pixel can then be compared to a threshold level. If a significant deviation is present, then pixel 106 is recorded as a location of a potential defect. The amount of deviation that is considered significant will depend upon the type of application. For example, when analyzing coatings on a plastic fuel tank, a deviation of 0.3–0.4 degrees C. or greater may be significant for a 5 millimeter kernel size. As an additional comparison, the coating thermal profile 104 taken at time t1 can be compared to an expected coating thermal profile 105, which can be determined empirically or via calculation and which represents an ideal shell after a coating is applied and no defects are present. Additional thermal profiles at differing times t can also be taken for layer 1 and used in similar comparisons.

Moreover, additional comparisons can be made of thermal profile data for each layer that is added. In this example, after the second layer is applied, a second coating thermal profile data set 110 is obtained at time t1 after the shell and two layers are heated. This second coating data 110 can then be compared to first coating data 104 to determine whether significant deviations in corresponding pixels are present. The second coating thermal profile data 110 can also be compared to the shell thermal profile data 102 to determine if deviations are present. Moreover, the second coating thermal profile data 110 at time t1 can also be compared to the expected thermal profile data 105. In addition, an additional second coating thermal profile can be obtained at time t2 and this data can be compared to the second coating data 110 taken at time t1 to determine an absolute thermal contrast data set 112. This absolute thermal contrast data 112 can be compared to an expected thermal contrast 114 for coating 2 at time t2. In addition, a self referencing thermal contrast computation can be made on the pixel data 116 (data 116 represents the thermal profile data taken for layer 2 at time t2). In this example, the temperature T for each pixel 118 is compared to the temperatures T of the surrounding pixels 119 (e.g., by using the average or mean temperature of the pixels 119) to determine the thermal contrast of each pixel. If a significant deviation exists between the thermal contrast of a pixel and the allowable contrast, pixel 118 can be recorded as a potential defect location. The number of surrounding pixels 119 can be varied depending on the application, and, in some embodiments, pixel 118 may actually represent the average temperature of multiple smaller pixels.

The pixel location of the defect thus identifies the two-dimensional location of the defect. Once the various defect pixel locations are identified, the depth of the defect can be calculated to provide a three dimensional identification of the defect location. For example, knowing thermal contrast and the time of the thermal profile where a defect was noted, the equation discussed above can be utilized to determine the defect depth. Thus, the time when a thermal contrast occurs after heating can indicate the depth of the defect detected. As an alternative, the above equation relating time to thermal reflection signal could be utilized to determine the depth of the defect.

The foregoing description of the various embodiments and examples has been presented for the purposes of illustration and description. It is not intended to be exhaustive or to limit the invention to the precise form disclosed. Many alternatives, modifications and variations will be apparent to those skilled in the art of the above teaching. For example, the systems and methods of the present invention may be applied to a variety of coatings in a multitude of applications outside of the automobile coating method. Accordingly, while some of the alternative embodiments of various elements, systems and methods for inspecting single and multilayered coatings have been discussed specifically, other embodiments will be apparent or relatively easily developed by those of ordinary skill in the art. Accordingly, the inventive aspects are intended to embrace all alternatives, modifications and variations that have been discussed herein, and others that fall within the spirit and broad scope of the claims.

What we claim is:

1. A method for detecting defects in coatings comprising the steps of:
    a) applying a first coating to a surface;
    b) modifying the temperature of the surface and coating;
    c) creating a thermal profile for said surface and said first coating by measuring a temperature parameter at each of a plurality of localized areas;
    d) for each localized areas, calculating a change parameter for the particular localized area by comparing the temperature parameter for the particular localized area to at least one value corresponding to the temperature parameters of localized areas surrounding the particular localized area, wherein the surrounding localized areas correspond to less than the entire thermal profile such that the at least one value changes dependent upon the particular localized area; and
    e) locating at least one defect by identifying at least one change parameter deviating from an acceptable level.

2. The method for detecting defects in coatings as recited in claim 1, further comprising the steps of:
    a) measuring a thermal profile of said surface to create a thermal signature;
    b) taking a first measurement of amount of radiation emitted from said surface and said first coating;
    c) comparing said radiation emitted to said thermal signature;
    d) applying a second coating to said first coating:
    e) creating a temperature differentiation between said surface, said first coating and a second coating;
    f) taking a second measurement of amount of emitted radiation from said surface and said first and second coatings; and
    g) comparing said first measurement to said second measurement.

3. The method for detecting defects in coatings as recited in claim 1, further comprising the step of identifying the three-dimensional location of said defects.

4. The method for detecting defects in coatings as recited in claim 1, further comprising the step of correcting a defect located.

5. The method for detecting defects in coatings as recited in claim 1, further comprising the step of changing, in real time, the operation of an application apparatus upon location of a defect.

* * * * *